(12) United States Patent
Henderson et al.

(10) Patent No.: US 11,578,303 B2
(45) Date of Patent: Feb. 14, 2023

(54) METHOD AND SYSTEM FOR PROCESSING A BIOLOGICAL SAMPLE

(71) Applicant: GENEA IP HOLDINGS PTY LIMITED, Sydney (AU)

(72) Inventors: Chester Henderson, Preston (AU); Ben Hobbs, Box Hill (AU); John McCormack, Warrandyte (AU); Benedict Stewart-Steele, Richmond (AU); Andrew C. Jenkins, Box Hill (AU); Sam Gason, Box Hill (AU); Eduardo Vom, Box Hill (AU); Susanna Brandi, Sydney (AU); Teija Tuulikki Peura, Erskineville (AU)

(73) Assignee: GENEA IP HOLDINGS PTY LIMITED, Sydney (AU)

( * ) Notice: Subject to any disclaimer, the term of this patent is extended or adjusted under 35 U.S.C. 154(b) by 752 days.

(21) Appl. No.: 16/481,878

(22) PCT Filed: Jan. 31, 2018

(86) PCT No.: PCT/AU2018/000007
§ 371 (c)(1),
(2) Date: Jul. 30, 2019

(87) PCT Pub. No.: WO2018/140999
PCT Pub. Date: Aug. 9, 2018

(65) Prior Publication Data
US 2019/0390155 A1    Dec. 26, 2019

(30) Foreign Application Priority Data

Jan. 31, 2017   (AU) ................................ 2017900270

(51) Int. Cl.
*C12M 1/00*       (2006.01)
*A61B 17/43*      (2006.01)
(Continued)

(52) U.S. Cl.
CPC ............. *C12M 47/04* (2013.01); *A61B 17/43* (2013.01); *B01L 3/508* (2013.01); *C12M 41/46* (2013.01);
(Continued)

(58) Field of Classification Search
CPC ....... C12M 47/04; C12M 41/46; A61B 17/43; B01L 3/508; B01L 2200/026;
(Continued)

(56) References Cited

U.S. PATENT DOCUMENTS 4,896,967 A   1/1990  Douglas-Hamilton et al.
5,028,526 A   7/1991  Deutsch
(Continued)

FOREIGN PATENT DOCUMENTS

CA    2 752 218 A1   10/2004
EP      095882 B1     8/2003
(Continued)

OTHER PUBLICATIONS

International Search Report and Written Opinion, PCT/AU2018/000007, dated May 22, 2018 (21 pp.).
(Continued)

*Primary Examiner* — Jennifer Wecker
*Assistant Examiner* — Oyeleye Alexander Alabi
(74) *Attorney, Agent, or Firm* — Eversheds Sutherland (US) LLP

(57) ABSTRACT

The present application is directed to the processing of a biological sample into its constituent components for use in ART and includes introducing a sample into a first volume disposed adjacent a second volume including buffer solution, wherein the first and second volumes are adapted for fluid communication therebetween, selectively separating the first volume from the second volume with a movable closure member disposed therebetween, wherein the step of
(Continued)

selectively separating the first volume from the second volume includes moving the closure member so that a fluid communication aperture is formed by one or a combination of the closure member or the closure member in combination with the first and second volumes to allow fluid communication between the first volume and the second volume such that motile cells migrate from the sample in the first volume to the buffer solution in the second volume.

19 Claims, 31 Drawing Sheets

(51) Int. Cl.
*B01L 3/00* (2006.01)
*C12M 1/34* (2006.01)
(52) U.S. Cl.
CPC . *B01L 2200/026* (2013.01); *B01L 2200/0647* (2013.01); *B01L 2200/0652* (2013.01); *B01L 2300/04* (2013.01); *B01L 2300/0663* (2013.01); *B01L 2300/0861* (2013.01)
(58) Field of Classification Search
CPC ..... B01L 2200/0647; B01L 2200/0652; B01L 2300/04; B01L 2300/0663; B01L 2300/0861; B01L 2300/0832; B01L 3/5082; A61D 19/022
See application file for complete search history.

(56) References Cited

U.S. PATENT DOCUMENTS

| 5,908,380 | A | 6/1999 | Zavos et al. |
| 6,391,654 | B1 | 5/2002 | Bateman |
| 6,426,213 | B1 | 7/2002 | Eisenson |
| 8,842,901 | B2 | 9/2014 | Ozcan et al. |
| 2002/0005354 | A1 | 1/2002 | Spence et al. |
| 2003/0165812 | A1 | 9/2003 | Takayama et al. |
| 2003/0196714 | A1 | 10/2003 | Gilbert et al. |
| 2006/0110821 | A1 | 5/2006 | Brickwood |
| 2006/0144707 | A1 | 7/2006 | Landers et al. |
| 2006/0270021 | A1 | 11/2006 | Takayama et al. |
| 2008/0187991 | A1 | 8/2008 | Takayama et al. |
| 2009/0101507 | A1 | 4/2009 | Aitken et al. |
| 2010/0291535 | A1 | 11/2010 | Yao et al. |
| 2011/0149287 | A1 | 6/2011 | Kislev et al. |
| 2011/0177547 | A1 | 7/2011 | Xia et al. |
| 2012/0052485 | A1 | 3/2012 | Shany et al. |
| 2012/0118740 | A1 | 5/2012 | Garcia et al. |
| 2013/0164838 | A1 | 6/2013 | Zech |
| 2014/0273179 | A1 | 9/2014 | Sharpe et al. |
| 2017/0205390 | A1* | 7/2017 | Shaked .............. G01N 15/1468 |

FOREIGN PATENT DOCUMENTS

| WO | 1994017742 A1 | 8/1994 |
| WO | 2002033047 A2 | 4/2002 |
| WO | 2003008931 A2 | 1/2003 |
| WO | 2003031564 A2 | 4/2003 |
| WO | 2010/056755 A2 | 5/2010 |
| WO | 2012032165 A1 | 3/2012 |
| WO | 2012162181 A2 | 11/2012 |
| WO | 2013129947 A1 | 9/2013 |
| WO | 2014006043 A2 | 1/2014 |
| WO | 2014/043635 A1 | 3/2014 |
| WO | 2014/177157 A1 | 11/2014 |
| WO | 2016063199 A1 | 4/2016 |
| WO | 2016178234 A1 | 11/2016 |

OTHER PUBLICATIONS

Seaforia™ Sperm Separation System, LotusBio, http://www.lotusbio.com/index.html?page=37 (2 pp.).
Fertile®, Microfluidic Sperm Sorting Chips, Koek Biotechnology, http://koekbiotech.com/fertile/ (7 pp.).
Fertile Plus®, Microfluidic Sperm Sorting Chips, Koek Biotechnology, http://koekbiotech.com/fertile-plus/ (8 pp ).
Fertile Ultimate®, Microfluidic Sperm Sorting Chips, Koek Biotechnology, http://koekbiotech.com/fertile-ultimate/ (9 pp.).
QSperm: Technology to help couples get pregnant faster, MaRS Innovation, http://marsinnovation.koazoa.com/wp/tag/qsperm/. May 16, 2014 (3 pp.).

* cited by examiner

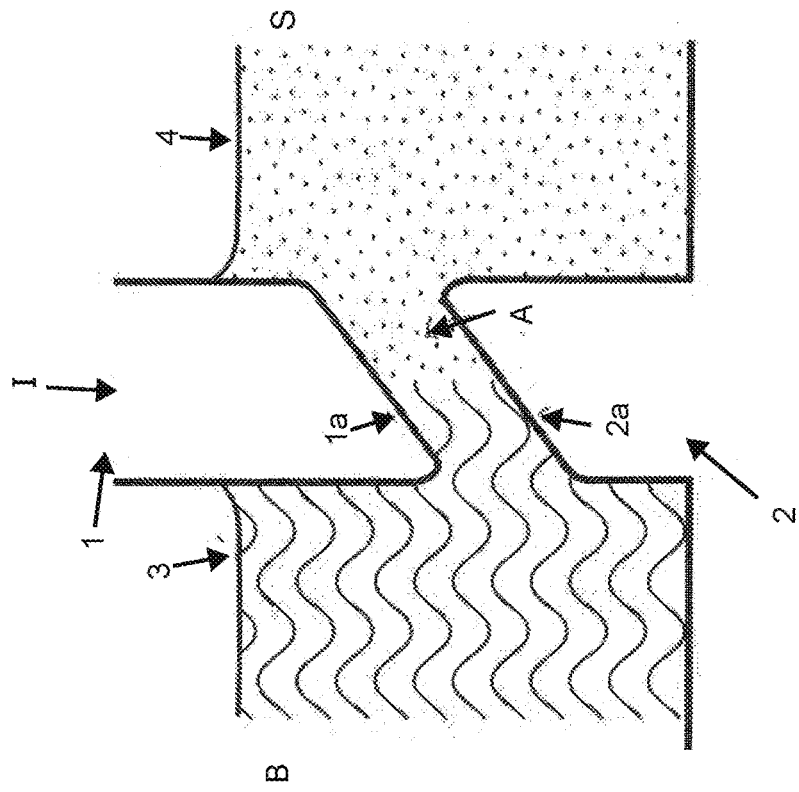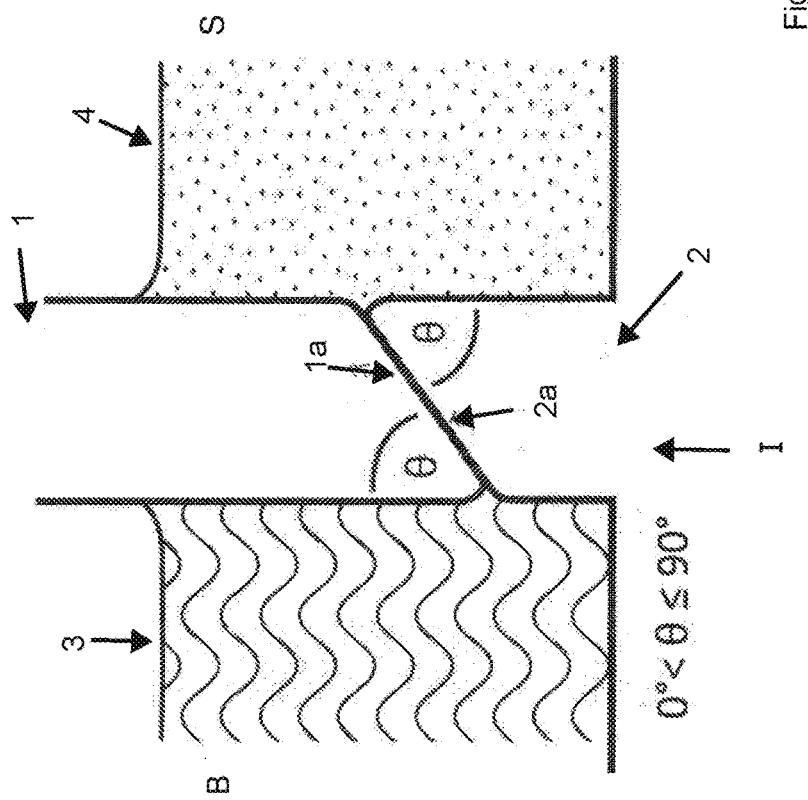
Figure 3

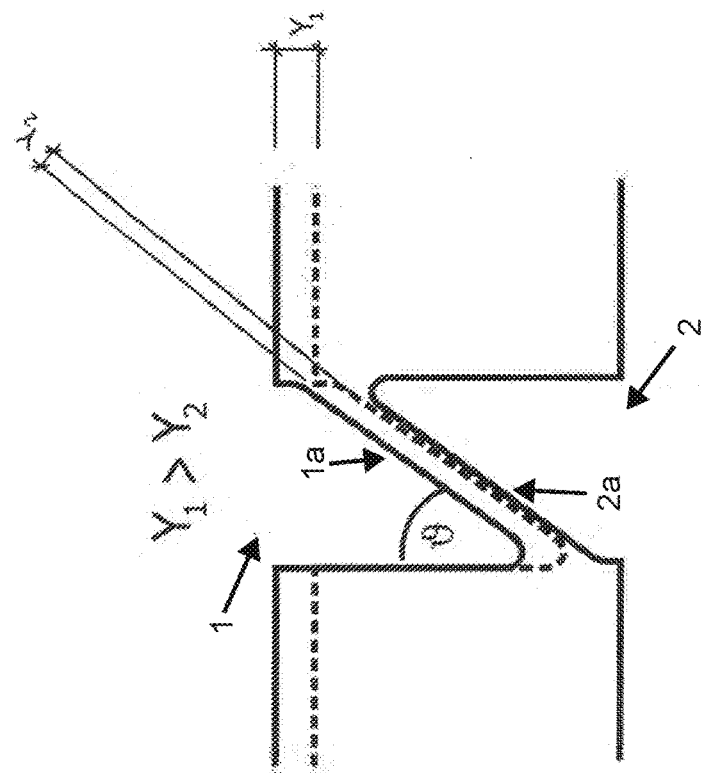
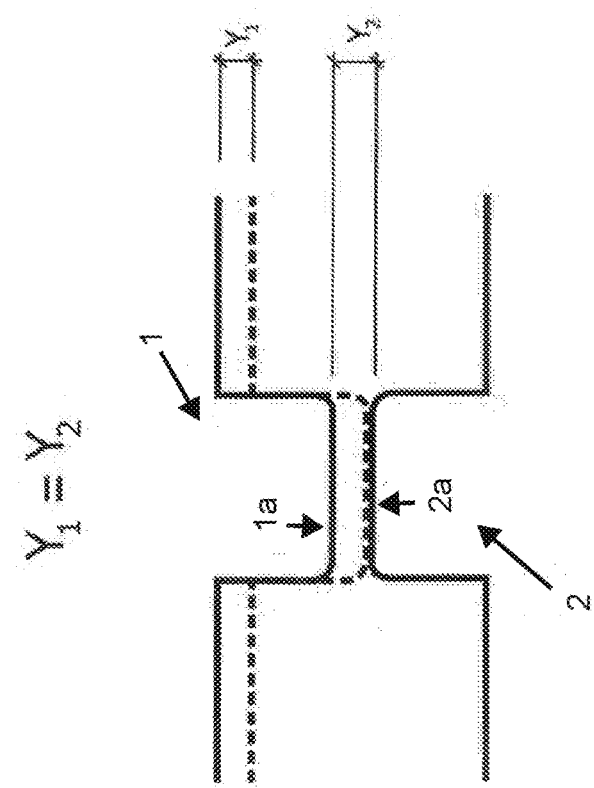
Figure 4

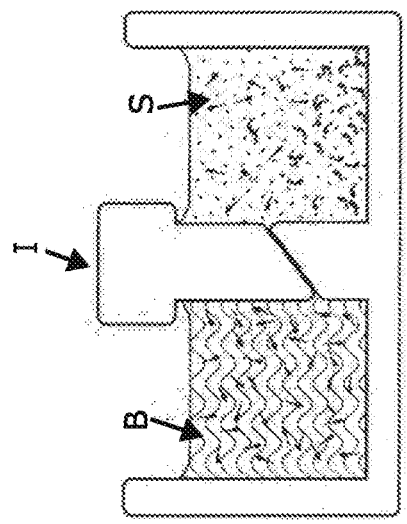
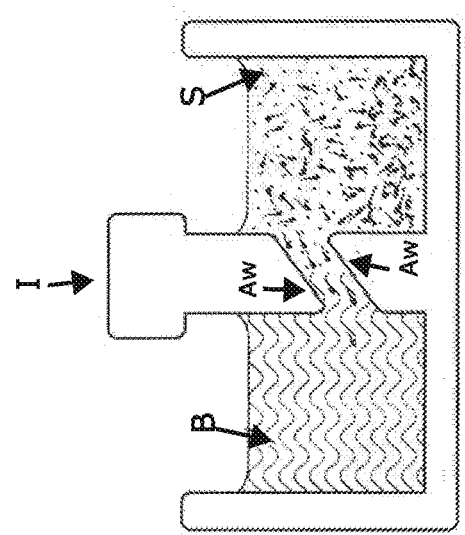
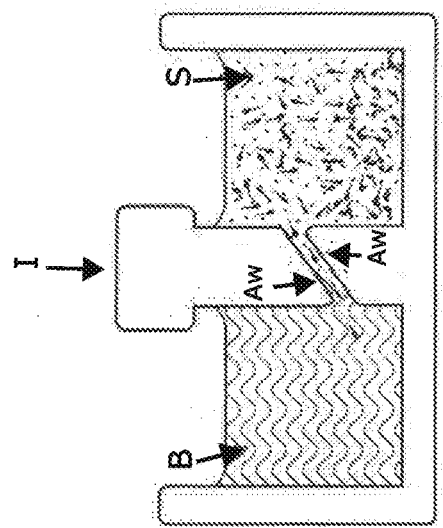
Figure 5

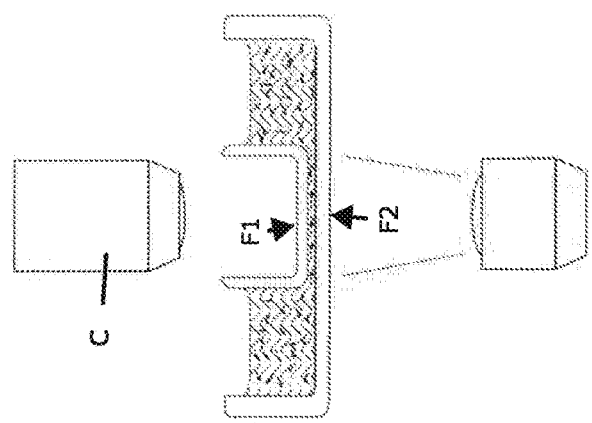
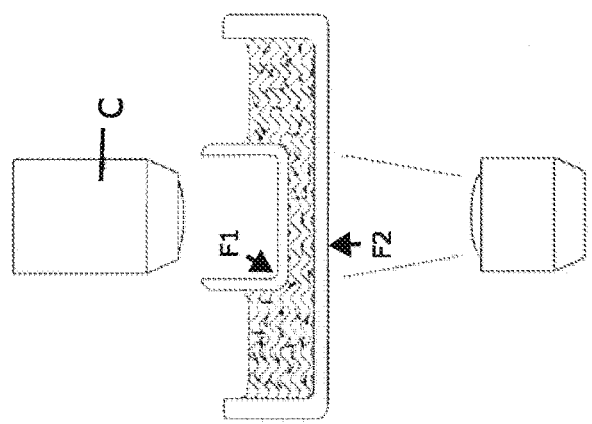
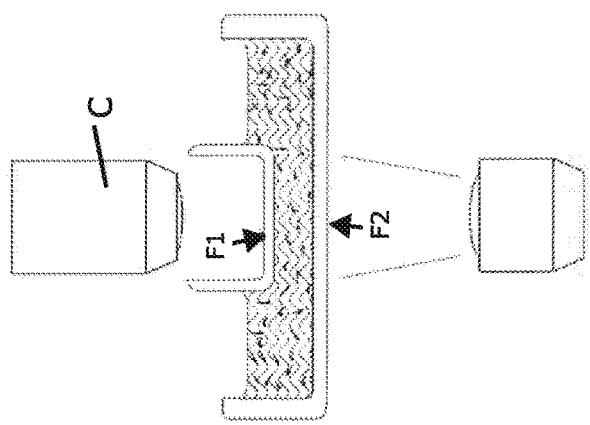
Figure 6

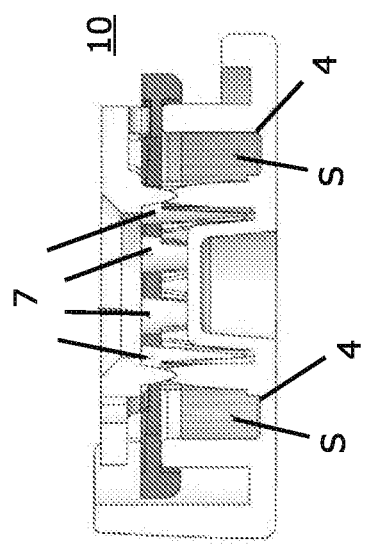
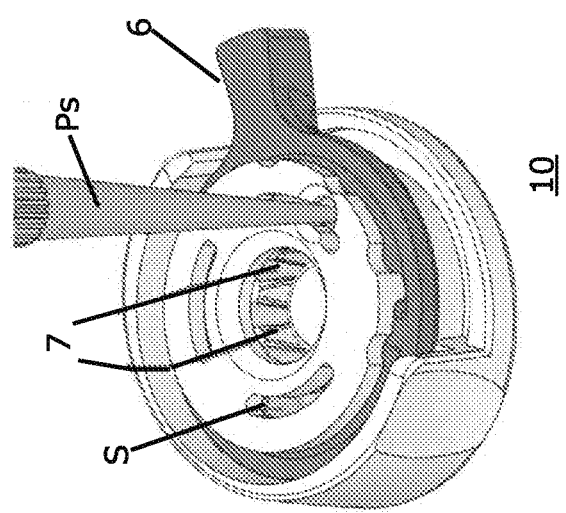
Figure 7a
Figure 7b

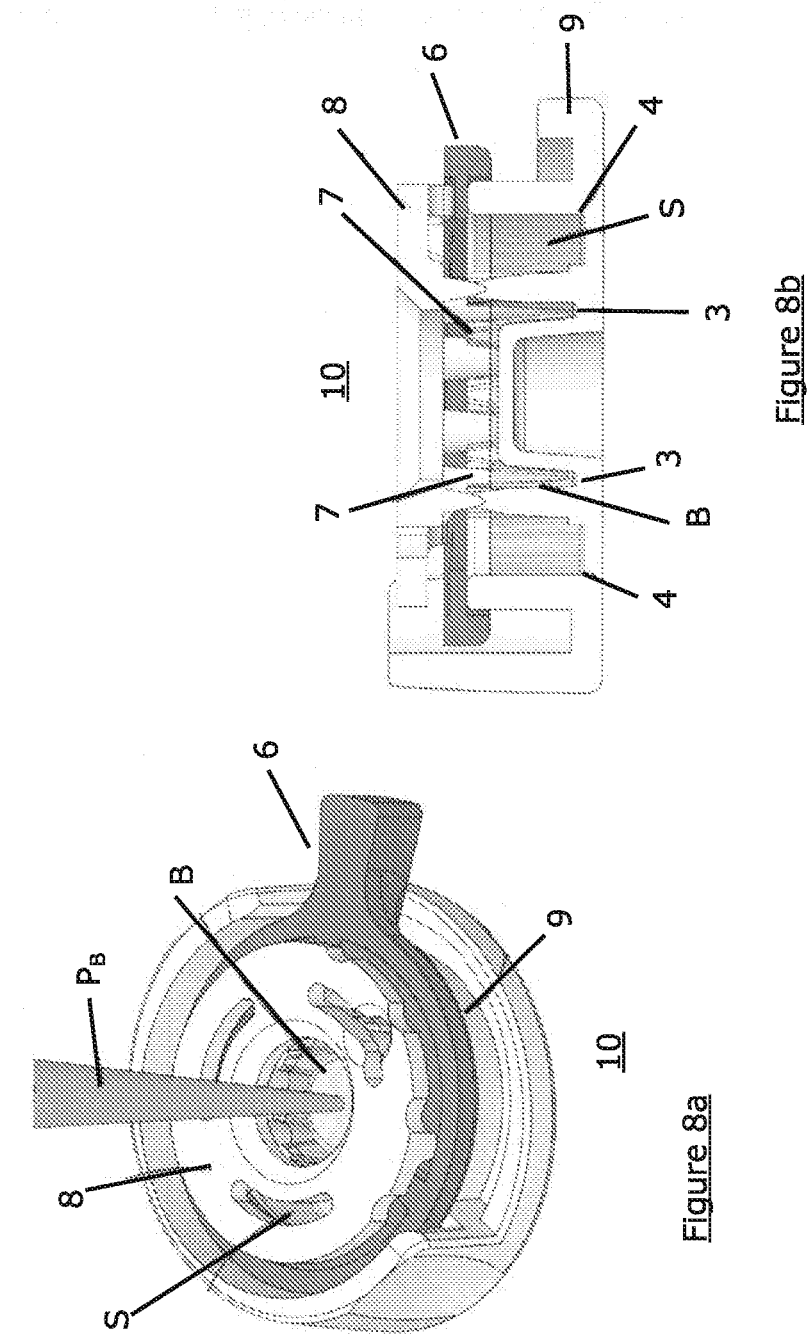

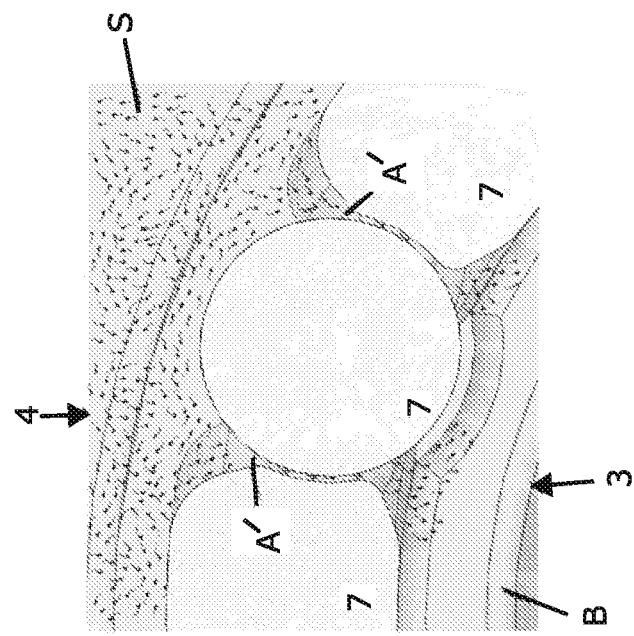
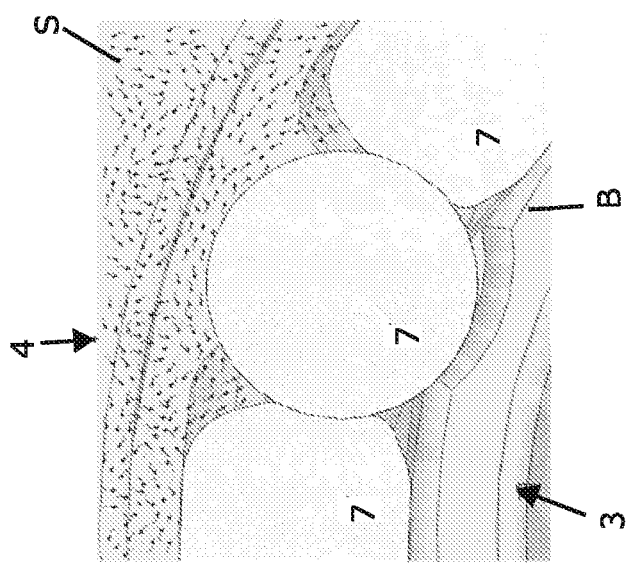
Figure 10b
Figure 10a

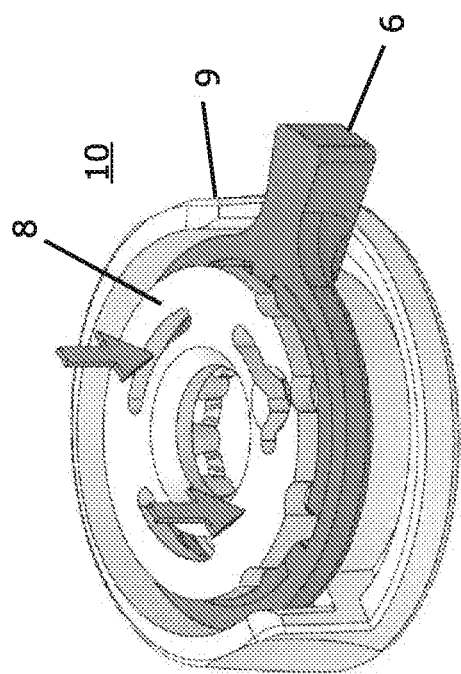
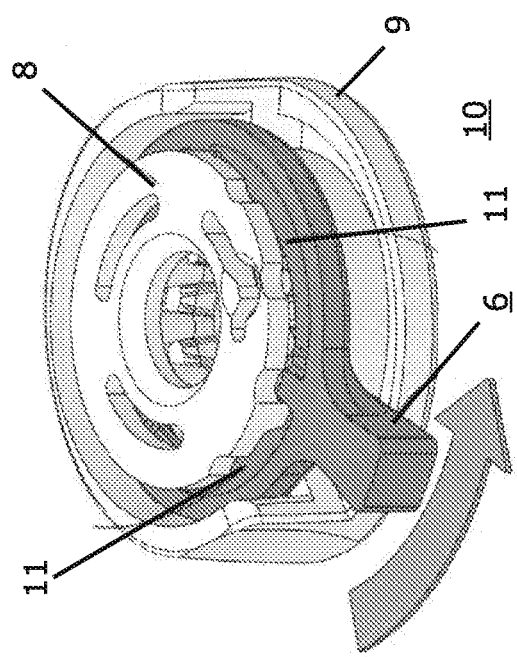
Figure 11a
Figure 11b

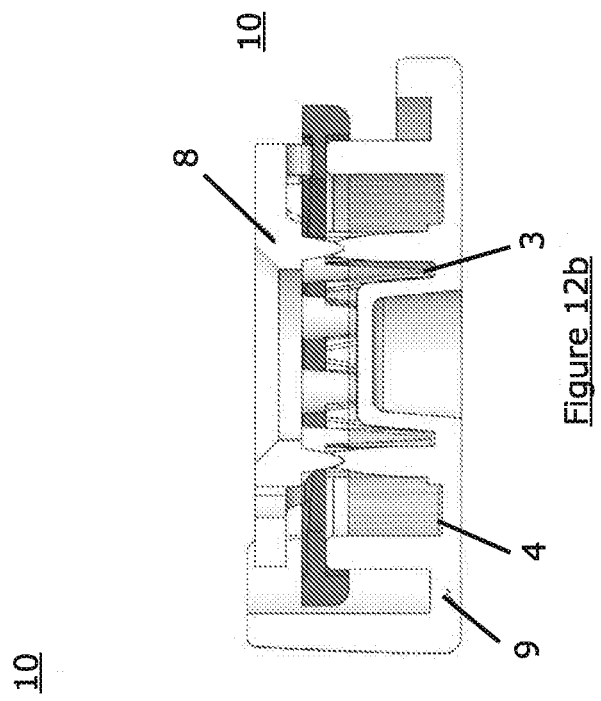
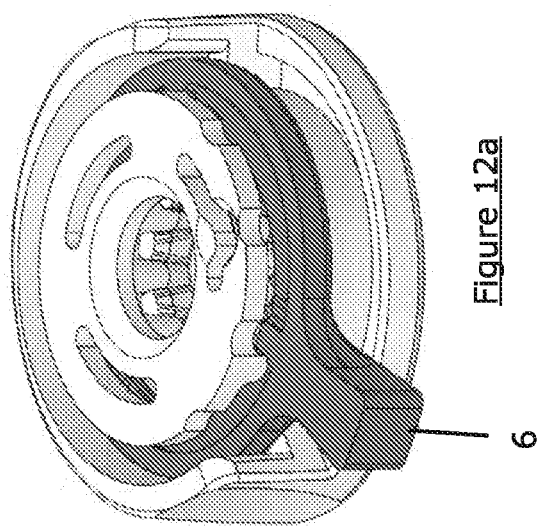
Figure 12b
Figure 12a

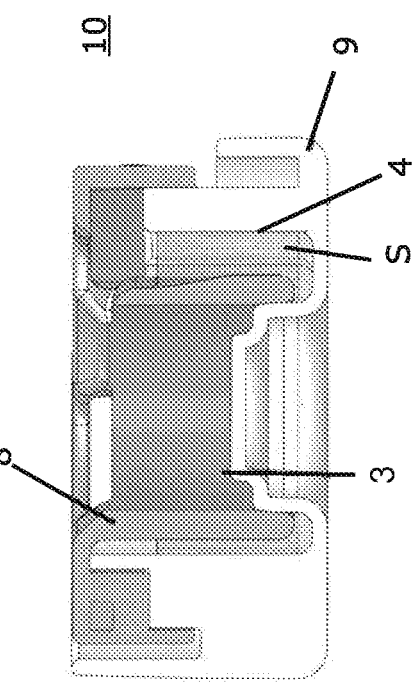
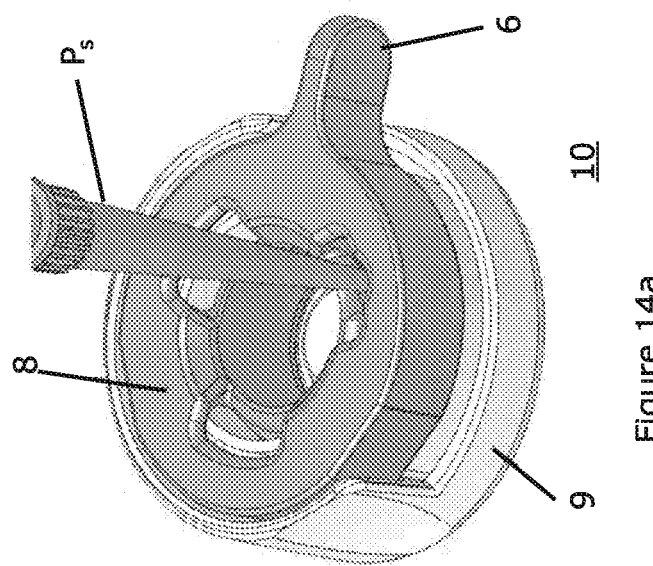
Figure 14a
Figure 14b

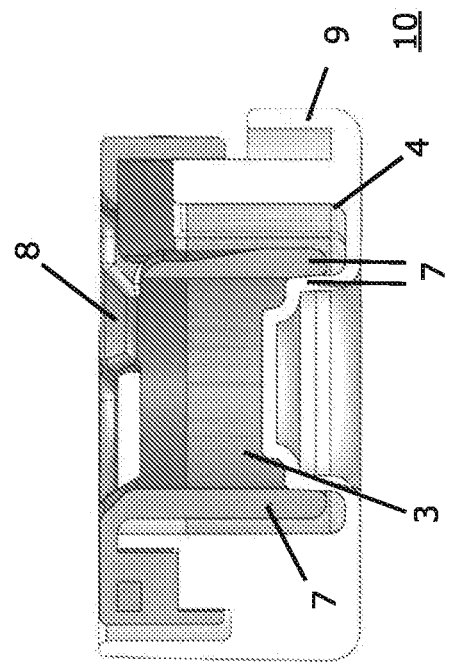
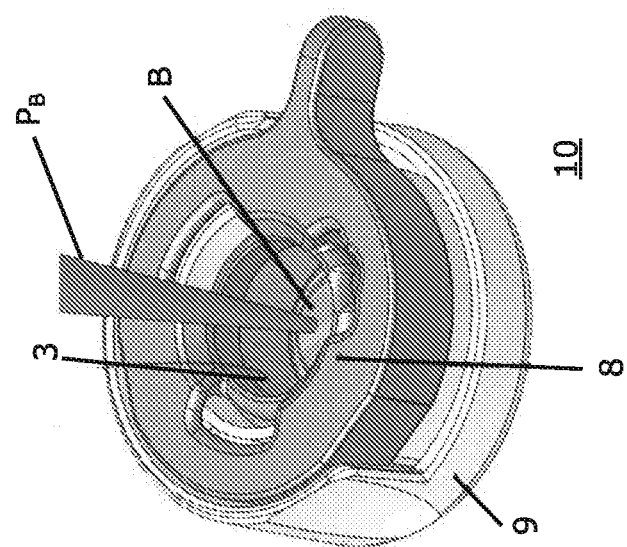
Figure 15a
Figure 15b

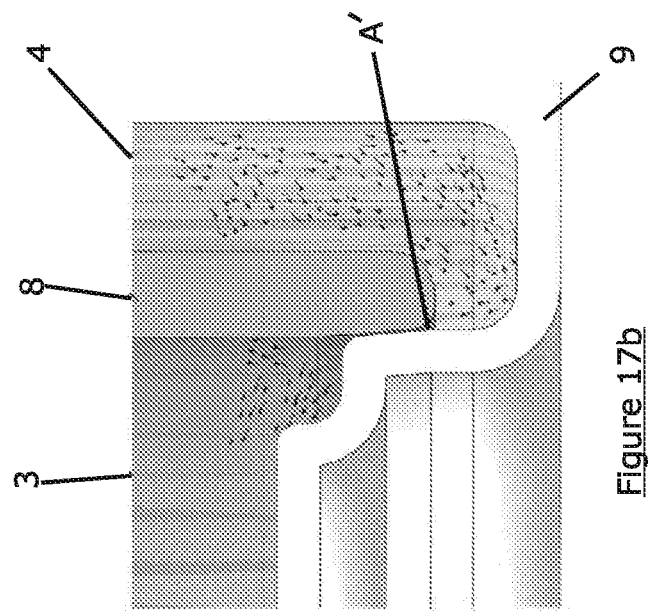
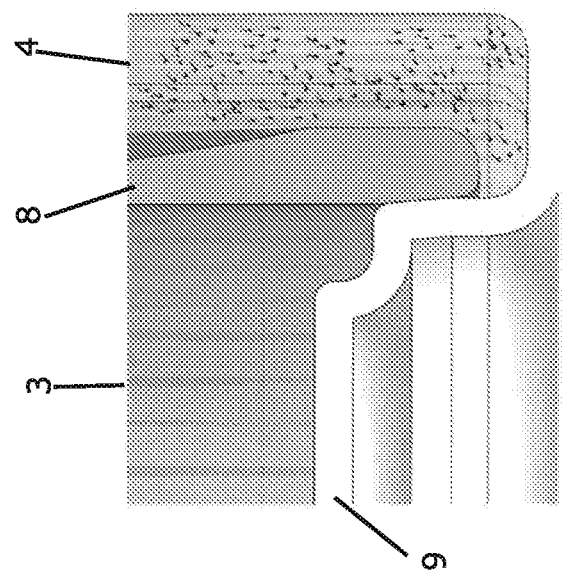

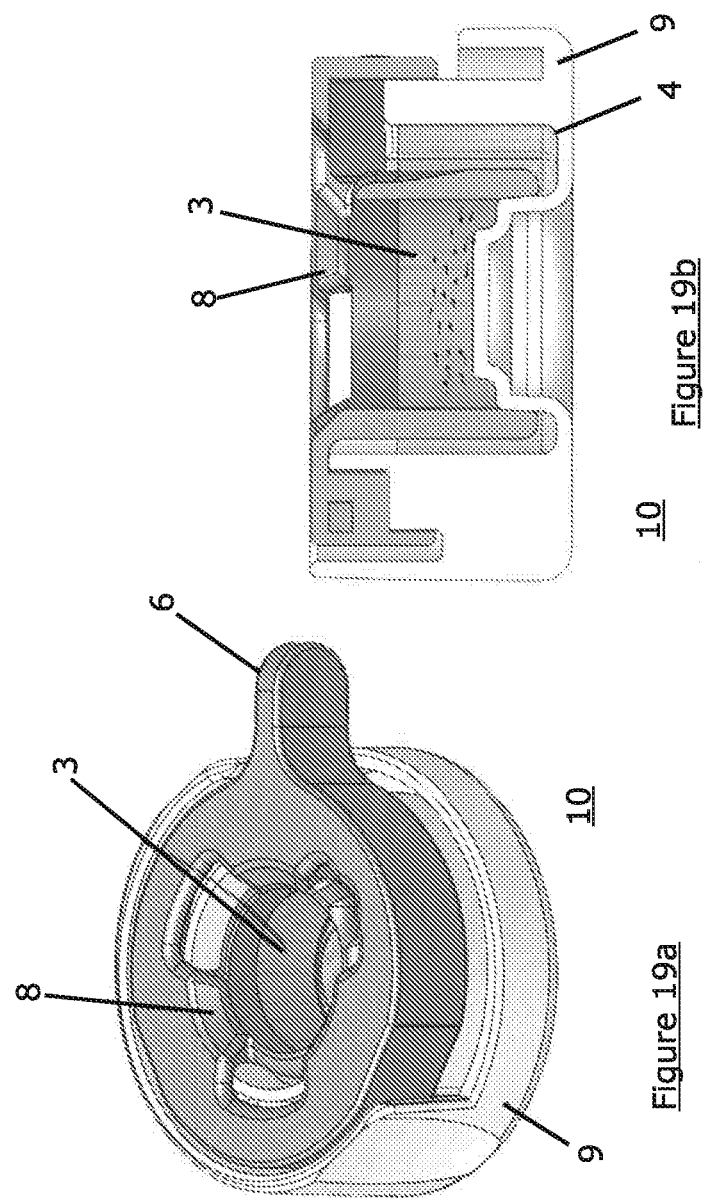

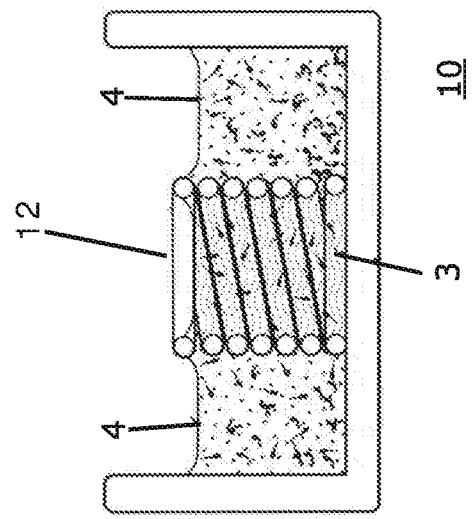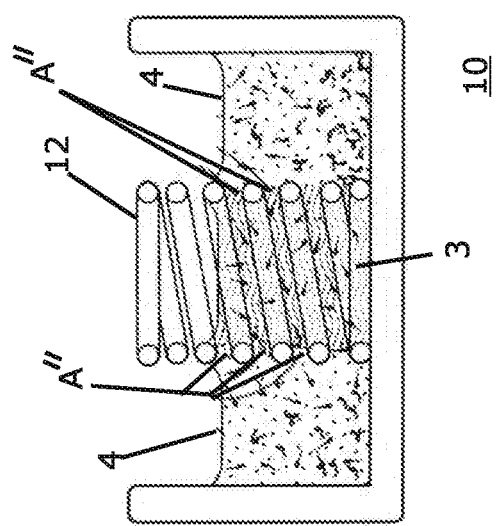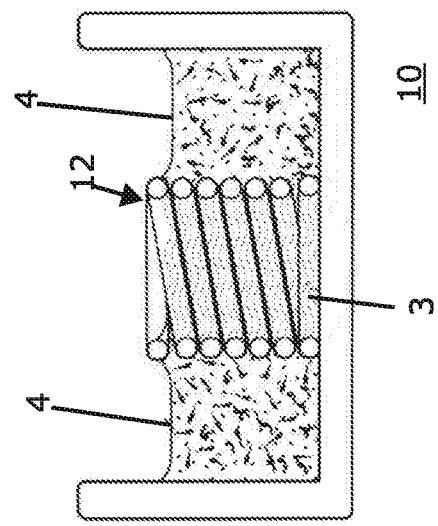
Figure 21

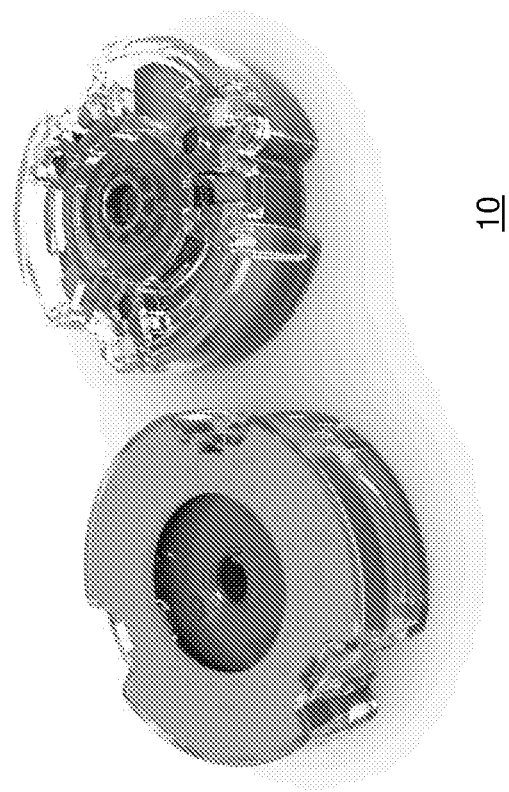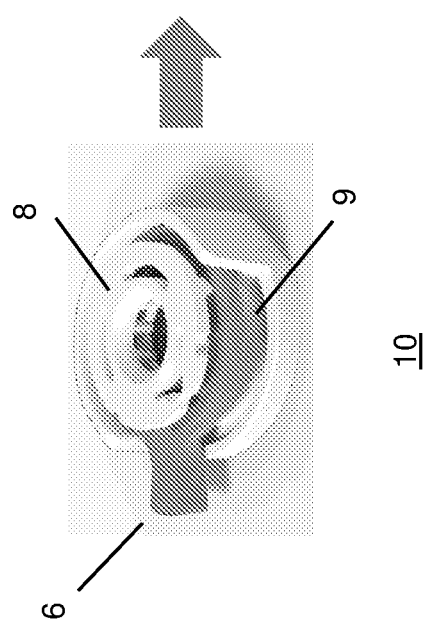
Figure 27

METHOD AND SYSTEM FOR PROCESSING A BIOLOGICAL SAMPLE

RELATED APPLICATIONS

This application claims priority to Australian Provisional Patent Application No. 2017900270 in the name of Genea IP Holdings Pty Ltd, which was filed on 31 Jan. 2017, entitled "Method and System for Processing a Biological Sample" and the specification thereof is incorporated herein by reference in its entirety and for all purposes.

FIELD OF INVENTION

The present invention relates to the field of assisted reproductive technologies (ART) and may be suitable for use in a number of fields including Human Fertility, Animal Breeding, Assisted Reproductive Technologies (ART) research (human and animal) and, Sperm banking. In one form, the invention relates to a method, system and apparatus for processing a biological sample into its constituent components for use in ART. The present invention is applicable for use with any biological sample containing motile cells or organisms, and it will be convenient to hereinafter describe the invention in relation to the processing and separation of motile sperm from a human semen sample, however it should be appreciated that the present invention may not be limited to that use, only.

BACKGROUND ART

Throughout this specification the use of the word "inventor" in singular form may be taken as reference to one (singular) inventor or more than one (plural) inventor of the present invention.

It is to be appreciated that any discussion of documents, devices, acts or knowledge in this specification is included to explain the context of the present invention. Further, the discussion throughout this specification comes about due to the realisation of the inventor and/or the identification of certain related art problems by the inventor. Moreover, any discussion of material such as documents, devices, acts or knowledge in this specification is included to explain the context of the invention in terms of the inventor's knowledge and experience and, accordingly, any such discussion should not be taken as an admission that any of the material forms part of the prior art base or the common general knowledge in the relevant art in Australia, or elsewhere, on or before the priority date of the disclosure and claims herein.

In Assisted Reproductive Technologies (ART), including clinical processes such as, for example, in vitro fertilisation (IVF), intracytoplasmic sperm injection (ICSI) and intra-uterine insemination (IUI), semen samples donated by the intended father are required to be processed to make them suitable for use. The main purpose of this processing is the removal of seminal plasma constituents that have negative impact on sperm viability and function. In vivo the seminal plasma is ordinarily removed during the sperm passage through the female reproductive tract. In addition to separating the plasma, the processing of semen samples aims for concentration and enrichment of the most viable and functional sperm population from the original semen sample, manifested by their motility.

Currently most widely used sperm processing methods include density gradient centrifugation (DGC) and so-called swim-up methods, although some other methods have also recently entered the markets.

With reference to FIG. 1, in the DGC method, a neat semen sample is placed into a centrifuge tube on top of two layers of colloidal suspension of silica particles in buffer. The upper phase or top layer consisting of lower concentration of particles, for example 45%. The lower phase or bottom layer consisting of higher particle concentration, for example 90%. The tube is then centrifuged, typically for 20 minutes at 1,600 rpm, allowing sperm to move through the 'upper phase' and 'lower phase' layers according to their properties, resulting in viable motile sperm ending up at the bottom of the tube, dead cells and debris within and/or between the silica layers, and seminal plasma remaining at the top of the tube. Several commercial silica compounds are available for this purpose, including for example Gems™ Sperm Wash Gradient Set (Genea Biomedx), SupraSperm™ (Origio), SpermGrad™ (Vitrolife) and many others. Following this step the motile sperm needs to be washed with sperm medium, sperm buffer or even fertilization medium via centrifugation at least once more to remove remnants of the silica compound.

DGC has advantages in that it provides for separation of motile sperm, removal of immotile sperm, debris and seminal plasma and it can also accommodate variable sample volumes for processing. However, DGC also has disadvantages in as much as there can be limited separation of morphologically abnormal sperm. Other disadvantages include a risk of user error in handling, variability of results, exposure to potentially harmful substances in the silica reagent, unwarranted effects of centrifugal forces, long processing times and the requirement for moving sample across several containers during different steps of the process. Nonetheless, DGC is currently the most common industry practice.

With reference to FIG. 2, in the swim-up method, a liquefied semen sample comprising neat semen is carefully placed at the bottom of a centrifuge tube containing sperm medium or buffer and left to sit in an incubator at a temperature of 37° for about an hour, during which time the motile sperm ie viable spermatozoa literally swims up the tube. The top layer of the media containing the motile sperm is then collected, leaving seminal plasma, dead sperm and debris behind. This collected portion is often centrifuged once more to concentrate the preparation, as sperm is usually needed in high concentration for the final processing step.

The swim-up method for sperm processing has advantages of being simple because it does not require complicated consumables or reagents. Further, variable sample volumes may be processed. However, there are disadvantages, for example, in that the sample cannot be left in the tube for extended periods due to its unfettered exposure to seminal plasma, prolonged exposure to which after ejaculation is known to diminish fertilizing capacity of human spermatozoa. Furthermore, it can be prone to the risk of user error, it has long processing time, it requires sample transfer across several containers during the different steps of the process and when the centrifugation step occurs sperm is exposed to the unwarranted effects of centrifugal forces. It is also a labour-intensive manual process. Nonetheless, the swim-up method is also current industry practice.

The problems encountered with both the DGC and swim-up methods relate to complexity and length of the process. Both require movement of the semen sample from the initial sample container through several different containers (and sub-containers for sub-samples) before reaching the IVF/ICSI dish or IUI catheter. Each such movement increases the risk of sample damage, loss of traceability, contamination, and requires a manual handling step as well as an associated double-witnessing/automatic witnessing step to ensure correct ID traceability throughout the process. The duration of the required procedures varies from 40 minutes to over an hour, adding complexity to the laboratory work flows as well as tying up laboratory equipment and space. The nature of the processes alternating between hands-on activities and waiting periods complicates the workflows even further.

Most laboratories adhere to stringent requirements of handling only one sperm sample at a time in order to reduce the risk of mix-up, and because of this, bigger laboratories have to maintain several sperm processing stations, each with their own devoted equipment such as laminar flow hoods, pipette sets and sometimes also a centrifuge. The need for manual labour is also high due to many consecutive steps requiring not only the time resources of the operator, but in many cases also time resources of the second witness to ensure sample safety and traceability. This in turn has flow-on effects to other ART operations by requiring the witness to interrupt their tasks, thus increasing the overall risk of operator error.

The large component of manual handling also makes the process susceptible for human error and variation resulting from different skill levels of the operators. The complexity of the process also calls for a large number of reagents and consumables to be used for the process, which involves further inherent stock managing, consumable and media risks and cost implications.

In addition, it has been shown that the DGC method may cause DNA damage in sperm, which in turn may have impact on not only sperm viability and functionality, but also on embryo development and possibly resulting pregnancy given that sperm DNA represents 50% of the genome of the embryo.

Some recent sperm processing systems rely on standardisation of some aspects of the previous methods, such as the swim-up-based system Seaforia™ with specifically designed consumables and a warming station, or likewise the swim-up based RI MSC™ sperm separation tube. The Seaforia™ system (described at the following Internet resource link http://www.lotusbio.com/index.html-?page=37) has the advantages of a controlled environment, ease of use and utilises standardised volumes but disadvantageously, it takes a long time, requires sample movement across several containers and requires a separate final output collection and analysis just like DGC and swim-up method do. As a new market entrant, information about clinical outcomes is limited. RI MSC is a simple procedure like swim-up but has drawbacks of having no active gating, is prone to user error, has a long process time, requires sample movement across several containers and also requires a separate final output collection and analysis. RI MSC has been in the market for several years.

Some systems use microfluidic designs that allow motile sperm to navigate through a microchannel and porous membrane such as; FERTILE® which is described at http://koekbiotech.com/fertile/, FERTILE PLUS® which is described at http://koekbiotech.com/fertile-plus/. There is also the FERTILE Ultimate® system, described at http://koekbiotech.com/fertile-ultimate/. These are all based on sperm travelling through a microfluidic channel from a place of deposition to a place of collection. The FERTILE® technique is simple and does not expose sperm to DGC reagents or centrifugal forces linked with causing DNA damage, but it has disadvantages in that it takes a long time, is impacted by the external conditions such as temperature and is costly. In addition, the FERTILE® system especially processes very low volumes and all systems require a separate final output collection and analysis. As the FERTILE® systems are new entrants to the market, information about clinical outcomes is limited.

Some known systems use filaments such as the Zech Selector™ instrumentation, described in US patent publication No. 2013/0164838. Likewise, Zech Selector™ is simple and does not expose sperm to factors promoting DNA damage but it has disadvantages in that it also takes a long time, requires fixed fluid volumes, and also requires a separate final output collection and analysis. Being a new market entrant, information about clinical outcomes is also limited.

Other known systems use a multitude of microfluidic channels, such as the QSperm system, which however has not reached commercial launch as yet. It is described at http://marsinnovation.koazoa.com/wp/tag/qsperm/.

Further known systems involve electrophoresis-based technologies relying on sperm selection in an electronic current based on their membrane potential. The expected advantages of these methods include that sperm are not exposed to known factors promoting DNA damage, and the technique may be amenable to be undertaken over a short time. However, there are unknown effects of electrophoresis reagents and processes upon sperm and these require complicated instruments, consumables and reagents. Also, none of these systems have reached commercial launch yet and information about clinical outcomes is not available or is very limited, being experimental only.

A number of other specific prior art systems are noted below.

PCT Publication No. WO 2012/162181 in the name of The Brigham And Women's Hospital, Inc. entitled, "Analysis and Sorting of Motile Cells" discloses a method for sorting motile cells including introducing an initial population of motile cells into an inlet port of a microfluidic channel, the initial population of motile cells having a first average motility; incubating the population of motile cells in the microfluidic channel; and collecting a sorted population of motile cells at an outlet port of the microfluidic channel. The sorted population of motile cells has a second average motility higher than the first average motility.

PCT Publication No. WO 2013/129947 in the name of Auckland Uniservices Limited entitled "Method and Apparatus for the Isolation of Motile Sperm" discloses the use of 'edge-trained' motile sperm and is directed to a method and system for separating motile and nonmotile sperm which comprises delivering a fluid containing sperm into a microvolume at least partially defined by a wall which includes a wall termination or a change in angle away from the microvolume that is noted as being a wall termination, and allowing at least some motile sperm to move along said wall and to exit the microvolume by changing direction away from the microvolume at or near the wall termination, to or towards collection of motile sperm. In broad terms in another aspect the invention comprises a method and apparatus for separating motile and non-motile sperm which comprises delivering a fluid containing the sperm into a microchannel comprising a wall which includes a wall termination, allowing motile sperm to move in substantially no-flow conditions in the microchannel along the wall and to exit the microchannel by changing direction away from the microchannel at or near the wall termination, to or towards a collection reservoir, and recovery of fluid containing the sorted sperm from the collection reservoir.

U.S. Pat. No. 5,028,526 in the name of Alice Deutsch entitled "Method for Semen Analysis" discloses a method for the separation of seminal plasma from semen by means of a membrane. The invention also includes a method for the determination of enzymes such as acqrosin and other components of semen.

United States Patent Publication No. US 2006/0270021 to Shuichi Takayama, et. al entitled "Integrated Microfluidic Sperm Isolation and Insemination Device" discloses an integrated microfluidic sperm isolation and oocyte insemination device, which provides the opportunity to perform in vitro insemination with motility enhanced sperm samples and with minimal manipulation of fragile oocytes. Sperm sorting is performed in a common sort channel wherein more mobile sperm swim across the interface between co-laminar flows of semen and media fluid.

United States Patent Publication No. US 2010/0291535 to Da-Jeng Yao, et al. entitled "Method Using Microfluidic Chip to Sort High Motility Sperm" discloses a method using a microfluidic chip to sort high motility sperm. Sperm and a medium are respectively injected into a microchannel of a microfluidic chip via several inlets. Owing to the characteristic of microfluidics, the sperm and the medium form a sperm laminar flow and medium laminar flow in the microchannels; the sperm laminar flow and the medium laminar flow are parallel to each other. The higher motile sperm may pass through at least one laminar flow within a limited time, whereby different motility levels of sperm can be respectively collected from different outlets.

United States Patent Publication No. US 2012/0118740 to The Regents of The University of California entitled "Methods and Devices for Sorting Cells and Other Biological Particulates" discloses an optical pattern-driven light induced dielectrophoresis (DEP) apparatus and separation methods are described which provide for the manipulation of particles or cells and selection based on traits correlated with the DEP response. Embodiments of the apparatus use DEP electric field patterns in combination with microfluidic laminar flows to measure response, separate, segregate and extract particles from heterogeneous mixtures according to the relative response of the particles to one or more DEP fields without damaging living cells. The methods are particularly suited for selecting and extracting the best sperm and embryo candidates based on fitness for use with existing artificial reproduction procedures and excluding defective or non-viable gametes.

United States Patent Publication No US 2008/0187991 to The Regents of The University of Michigan, entitled "Process for Sorting Motile Particles from Less Motile Particles" discloses a technique in which motile particles are sorted from non-motile particles in a microfluidic sorting device wherein a stream of sort fluid containing motile and non-motile particles is caused to flow adjacent a media stream in non-turbulent fashion through a sort channel, during which flow motile particles cross the interface between the adjacent flow streams, entering the media stream, and forming a motile particle-depleted sort stream. The sorting devices are easily and inexpensively fabricated and have numerous uses, in particular, sorting of motile from non-motile sperm.

PCT Publication No. WO 2012/032165 to Josef Zech entitled "Method for Enrichment of DNA Strand Break-Free Spermatozoa and Reduction of Risks for Abnormalities and/or Aneuploidy" discloses a method for producing an enriched DNA strand break-free spermatozoa sample from a poor quality seminal fluid, wherein a selecting device which comprises two chambers and a bridge element is used and the method comprises placing a seminal fluid comprising at least 15% oligo-, at least 32% astheno-, and/or at least 4% teratozoospermia, based on the total amount of the spermatozoa in the seminal fluid, in the first chamber of the selecting device, filling the second chamber of the selecting device with a medium for receiving DNA strand break-free spermatozoa and connecting both chambers by a bridge element such that a fluid bridge between the first and second chamber occurs which allows the DNA strand break-free spermatozoa to move from the first to the second chamber.

United States Patent Publication No US 2009/101507 originally assigned to The University of Newcastle Research Associates Limited, entitled "Sperm Cell Separation By Electrophoresis" discloses a process for separating a sperm type from a sperm population by electrophoresis in a modification of a laboratory electric circuit for electrophoresis, which involves subjecting the sperm population to an electric potential such that a sperm type is separated from a sperm population through an ion-permeable barrier.

PCT Publication No. WO 1994/017742 to Josef Zech entitled "Device for Removing Sperm Cells from Seminal Fluid" discloses a device for in-vitro fertilization with a container for ova and a container for sperm cells, in which a capillary tube provides a liquid bridge between the containers. Preferably the liquid bridge extends between the ova container and a part which passes round its upper edge in a U-shaped fashion.

PCT Publication No. WO 2003/031564 to Josef Zech entitled "Device and Method for Selecting Locomotive Biological Species, Particularly Sperm Cells" discloses a device for selecting locomotive sperm cells, comprising a first chamber provided for accommodating a medium containing the species to be selected and a second chamber, which is separate from the first and provided for accommodating the selected species in another medium. A bridge element, which can be placed on the chambers and which has at least one flat-like channel. Said channel is formed by delimiting walls, extends from the first chamber to the second chamber when the bridge element is placed thereupon, and has an opening in the area of the first chamber and in the area of the second chamber. In addition, the channel can be filled with a medium, in which the locomotive biological species can move, whereby bringing the medium in the first chamber in contact with the medium in the second chamber.

PCT Publication No. WO 2014/006043 to Josef Zech entitled "Device for Spermatozoa Selection" discloses a first chamber configured to receive a first, seminal fluid; a second chamber configured to receive a second fluid, the second chamber being in fluid communication with the first chamber by means of at least one duct having a first opening to the first chamber and a second opening to the second chamber; and a displacement means adapted to displace at least some of the first, seminal fluid towards the first opening.

U.S. Pat. No. 6,391,654 to Genosis Limited entitled "Separation and Detection of Spermatozoa" discloses a kit for testing male fertility comprising a vessel, a base unit, a liquid supply containing liquid and two filters. The first filter is a sample separation filter which forms a hindrance to transmission of spermatozoa. The second filter of the kit is a spermatozoa detection filter comprising a reagent for identifying spermatozoa. Activation of the kit is prevented until a transport medium, such as the liquid, fills a gap allowing spermatozoa to transmit to a detection zone. The kit may be of one-piece construction and utilizes a thin piece of filter material to separate motile from non-motile spermatozoa.

United States Publication No. US 2006/0110821 to David Brickwood entitled "Devices for Motile Sperm Separation" discloses a vessel having an inlet port, an outlet port which is initially closed, a medium into which motile sperm in the sample can migrate into the vessel via the inlet, and an actuator, the operation of which opens the outlet, thereby allowing the medium to flow out of the vessel through the outlet. The medium in the vessel is initially prevented from flowing through the outlet, thus allowing an incubation period which allows motile sperm sufficient time to migrate from the sample into the medium before the medium leaves the vessel. The device preferably comprises a spermatozoa detector in communication with the outlet. In devices for separating sperm, capillary flow takes place through non-fibrous material, such as the space between sheets of closely-juxtaposed material.

United States Publication No. US 2012/0052485 to Lotus Bio (Nymphaea) Ltd. Entitled "Sperm Separation System" discloses a naturally based Sperm Separation System (SSS) for separation of at least a portion of sperm cell populations (SCP) within an original semen sample, such that an enriched SCP sample is obtained, comprising a sperm separation device, comprising a first chamber adapted to contain at least a portion of said original semen sample, said first chamber is characterized by predetermined 3D shape and volume, said first chamber is bounded by a rim such that said original sample is kept below said rim, a second chamber in physical communication with said first chamber and said rim, said second chamber is characterized by predetermined 3D shape and volume, said second chamber is adapted to reside said enriched SCP sample, incubation means, adapted to socket at least one of said cell separation device and to homogeneously thermoregulate the temperature within the same.

U.S. Pat. No. 5,908,380 to Zavos et al. entitled "Compartmentalized Zavos Sperm Swim-Up Column" discloses a device comprising a hollow, vertically supported column, having a closed lower end, and an open upper end. A lowermost or first conical member is arranged at the lowermost end of the column, the lowermost conical member having a lowermost periphery in sealing engagement with the bottom of the column. The first conical member has inclined side walls and a truncated uppermost portion defining a peripheral edge which is open within into the column. A second conical member having a lowermost periphery is also attached to the side walls of the column in a sealing manner therebetween. The second conical member also has tapered walls and a truncated uppermost portion defining a peripheral edge which is open to the inside of the column. The area between the inclined walls of each of the conical members and the inner wall of the column define a periconical area which comprises a compartment for collecting sperm prior to harvesting thereof.

PCT Publication No. WO 2014/043635 to President and Fellows of Harvard College discloses a microfluidic system which includes a microfluidic channel. The microfluidic channel includes a control layer substantially enclosed within a soft polymer, a cell covering element, and a flow channel between the cell-covering element and control layer enclosed within the soft polymer. The control layer is operable to move towards and exert a pressure on the cell-covering element. In the apparatus of WO 2014043635, cells start in one shared cell environment and then get separated. Cell movement can actually be stopped by the exerted pressure forcing a silicone control layer to interfere with the passing of cells in a flow path. The technique described is not based on motility of cells but more directed to flow cytometry where cells in suspension are hydrodynamically driven along a flow path with a focus on fluorescence and staining.

PCT Publication No. WO 2016/063199 to Ecole Polytechnique Federale De Lausanne discloses a microfluidic device for the culture, selection and/or analysis of sample organisms such as nematodes, as well as for other biological entities such as for instance animal embryos. The device features reservoirs, culture chambers and filtering systems allowing for the selection of specific populations/specimens of sample organisms, thus permitting long-term cultures thereof as well as phenotypic/behavioural analyses. This device also requires the use of pressure to operate upon the organisms in a chamber to pass them through a filtering means to a culture chamber.

PCT Publication No. WO 2010/056755 to Craig discloses a robotic microfluidic incubator system which has a thin transparent sidewall and close proximity of the embryo/oocyte/cultured cells to the sidewall allow close approach of a side view microscope with adequate focal length for mid to high power. The arrangement permits microscopic examination of multiple culture wells when arranged in rows (linear or along the circumference of a carousel). Manual or automated side to side movement of the linear well row, or rotation of the carousel, allows rapid inspection of the contents of each well. Automated systems with video capability also allow remote inspection of wells by video connection or Internet connection, and automated video systems can record oft-hours inspections or time lapse development in culture (i.e. embryo cell division progression, or axon growth in neuron cell cultures). As with WO 2014/043635 and WO 2016/063199, above, the device disclosed by Craig requires moving fluid media.

United States Publication No. US 2002/005354 to Spence et al discloses a microfabricated device for sorting cells based on a desired characteristic, for example, reporter-labelled cells can be sorted by the presence or level of reporter on the cells. The device includes a chip having a substrate into which is microfabricated at least one analysis unit. Each analysis unit includes a main channel, having a sample inlet channel, typically at one end, and a detection region along a portion of its length. Adjacent and downstream from the detection region, the main channel has a discrimination region or branch point leading to at least two branch channels. The analysis unit may further include additional inlet channels, detection points, branch points, and branch channels as desired. A stream containing cells is passed through the detection region, such that on average one cell occupies the detection region at a given time. The cells can be sorted into an appropriate branch channel based on the presence or amount of a detectable signal such as an optical signal, with or without stimulation, such as exposure to light in order to promote fluorescence. The apparatus of Spence uses channels with flowing fluids to interact with the microfabricated substrates and relies on reporters of cells and not the cells own movement.

Canadian patent publication No. CA 2752218 to Inguran, LLC., discloses apparatus for sorting stained particles in a fluid stream according to one or more characteristics of the particles. The fluid stream comprises: (A) a fluid delivery system for delivering a fluid stream containing the particles to a first location; (B) an electromagnetic radiation source for delivering a beam of electromagnetic radiation to the first location for exciting particles in the fluid stream to produce fluorescence emissions; (C) an epi-illumination optics system including a focusing lens, where the optics system is operable to direct the beam of electromagnetic radiation through the focusing lens in a forward direction along a beam axis intersecting particles in the fluid stream at said first location so that said particles pass through the beam, resulting in the fluorescence emissions from the particles being directed along said beam axis in a rearward direction; (D) a photodetector for detecting fluorescence emissions from the excited particles; and (E) a processor in communication with the photodetector to classify the particles according to the one or more characteristics based upon the fluorescence emissions of the particles and to sort the particles according to the classification of particles. This system may be applied to staining of sperm cells and subsequent selection under flow cytometry. It also requires moving fluid. In so far as sperm is concerned the system is directed to the characteristics of sperm chromosome content.

European patent No. EP 0958862 to AMS s.r.l. discloses a multiuse reactive-plate for analysis, particularly for direct analysis of whole blood or fluids containing any kind of particles or fragment. The multiuse reactive plate is able to carry out measurements of single analytes. In the system disclosed, fluids are moved by force and involve valves within the flow path.

PCT Publication No. WO 2002/033047 to Nexgenics Bioscience Corp. discloses an embryo support assembly, embryo support system, a method for maintaining the viability of a growing embryo, and a method for shipping a metabolically active embryo. In this apparatus, which uses valves for fluid flow, sperm is only referenced with respect to it being added to the eggs, as is, for fertilisation.

United States Publication No. US2003196714A1 to Gilbert et al discloses a microfluidic system which includes a bubble valve for regulating fluid flow through a microchannel. The bubble valve includes a fluid meniscus interfacing the microchannel interior and an actuator for deflecting the membrane into the microchannel interior to regulate fluid flow. The actuator generates a gas bubble in a liquid in the microchannel when a sufficient pressure is generated on the membrane.

United States Publication No. US 2014/273179 to Inguran, LLC. discloses a device in the form of a microfluidic chip. In particular, various features are incorporated into the microfluidic chip for aligning and orienting sperm in flow channels, as well as for separating selected subpopulations of sperm. Again, this device requires forced flow to move cells. It also is directed to determining sperm chromosome content.

United States Publication No. US 2011/177547A1 to Xia et al discloses a fluidic device which includes an arrangement of channels for introducing a sample containing particles of interest into a processing chamber. The chamber is in fluid communication with collecting channels via low-flow connection channels. Particles in the sample may be observed and diverted from the processing chamber by application of a motive force such as optical trapping into a collection channel. Once in the collection channel, particles can be collected, including by trapping in a porous matrix.

PCT Publication No. WO 2013/129947 to Auckland UniServices Limited discloses a method and apparatus for sorting motile sperm. This described system utilizes the phenomenon of 'edge-trained' motile sperm in which motile sperm with progressive motion that encounter a structure such as a wall will tend to turn and move along the wall in a direction depending on the initial approach angle of the sperm. With the use of this phenomenon the system involves delivering a fluid containing sperm (by way of pumping sperm into channels) into a microvolume at least partially defined by a wall which includes a wall termination or a change in angle away from the microvolume that is noted as being a wall termination, and allowing at least some motile sperm to move along said wall and to exit the microvolume by changing direction away from the microvolume at or near the wall termination, to or towards collection of motile sperm. In another aspect the described system comprises a method for delivering a fluid containing the sperm into a microchannel comprising a wall which includes a wall termination, allowing motile sperm to move in substantially no-flow conditions in the microchannel along the wall and to exit the microchannel by changing direction away from the microchannel at or near the wall termination, to or towards a collection reservoir, and recovery of fluid containing the sorted sperm from the collection reservoir. Specifically, the system as described is based on pumping sperm into channels, stopping, and letting them enter into empty side chambers, then flushing excess sperm away and allowing motile sperm to come back to mid-channels that form the chambers (or conversely; pump sperm to side chambers, flush mid channel and allow motile sperm to come to mid channel and flush again to collect).

PCT Publication No. WO 2003/008931 to Hvichia et al discloses a microscale cell separating apparatus which is able to separate cells on the basis of the size of the cells, interaction of the cells with surfaces of the apparatus, or both. The apparatus comprises a stepped or sloped separation element interposed between an inlet region and an outlet region of a void that can be filled with fluid. The void can be enclosed within a cover, and fluid flow through the void engages cells with the separation element. Only cells which have (or can deform to have) a characteristic dimension smaller than or equal to the distance between a step and the cover or body can pass onto or past a step. Modification of surfaces within the apparatus can also inhibit passage of cells onto or past the step. There is no teaching in this disclosure of its application to sperm or how that may be achieved.

US patent publication No. US 2003/0165812 to Takayama et al discloses a process and apparatus in which motile particles are sorted from non-motile particles in a microfluidic sorting device wherein a stream of sort fluid containing motile and non-motile particles is caused to flow adjacent a media stream in non-turbulent fashion through a sort channel, during which flow motile particles cross the interface between the adjacent flow streams, entering the media stream, and forming a motile particle-depleted sort stream. The sorting devices have use, in particular, for sorting of motile from non-motile sperm. The system described relies on sperm moving in a sheath fluid and traversing across fluids without any apertures or closures.

The following prior art relates to methods involving 'vision tracking' of sperm.

U.S. Pat. No. 8,842,901 to The Regents of The University of California entitles "Compact Automated Semen Analysis Platform Using Lens-Free On-Chip Microscopy" discloses a compact and light-weight lens-free platform to conduct automated semen analysis. The device employs holographic on-chip imaging and does not require any lenses, lasers or other bulky optical components to achieve phase and amplitude imaging of sperm a relatively large field-of-view with an effective numerical aperture of approximately 0.2. A series of digital image frames is obtained of the sample. Digital subtraction of the consecutive lens-free frames, followed by processing of the reconstructed phase images, enables automated quantification of the count, the speed and the dynamic trajectories of motile sperm, while summation of the same frames permits counting of immotile sperm.

U.S. Pat. No. 4,896,967 to Hamilton-Thorn Research entitled "Motility Scanner and Method" discloses an improved motility scanner for characterizing the motion of sperm, bacteria, particles suspended in flowing fluids and the like. The motility scanner includes an improved optical system, a source of illumination for the system and radiation sensing means including electronic image reversal means coupled to the system. A disposable specimen holder allows external loading thereof and its positioning on a heated specimen support. The illumination source functions as a collimator in directing all of the emanating illumination onto the specimen. Both directly transmitted light and light scattered by the specimen are received by an imaging lens and are both focussed thereby onto pixels of a light sensitive device. A movable plate provided with a retarding member is designed to be located at the plane conjugate to the plane of the small source aperture. The directly transmitted light is transmitted through the retarding member and/or the attenuating member. The light scattered by the specimen, however, travels for the most part through the plate in areas not covered by the retarding and/or attenuating members.

U.S. Pat. No. 6,426,213 to Progeny Systems, LLC entitled "Sperm Analysis System" discloses a sperm analysis system which has a sperm sample carrier and "reader" module. The sperm sample carrier includes: a shank defining a chamber with an opening for ingress and egress of a sperm sample; a manually operated pump for aspirating a sample of sperm into the chamber, and a plurality of distinct photon paths intersecting and passing through the chamber. The module includes: a processor responsive to an actuation signal from an operator, a photon source, e.g. a light source, energized by the processor in response to the actuation signal, for sending respective beams of photons through each of the photon paths, a plurality of photosensors, one for each photon path, each for producing a signal indicative of the occurrence and frequency of perturbations in the beam of photons passing through said each's respective photon path and communicating the signal to the processor, and an algorithm run by the processor for processing the plurality of photosensors signals to produce a quantified figure of merit indicative of the motility of sperm within the chamber.

United States Publication No. US 2011/0149287 to M.E.S. Medical Electronic Systems Ltd. entitled "Semen Analysis" discloses a method for measuring the total sperm concentration (TSC) in a sample including: placing the sample in a transparent container between a synchronically pulsed light source and a photodetector; and measuring the optical absorbance of the sample in the range of 800-1000 nm, the TSC of the sample being proportional to the absorbance. Further provided is a sampling device for use in optically analysing a biological fluid, a method for measuring motile sperm concentration (MSC) in a semen sample, a method of determining the average velocity (AV) of sperm cells and a system for analysing semen quality comprising means for measuring TSC, means for measuring MSC; and a video visualization system.

However, the outcome of sperm processing methods comprises a portion of washed, motility-selected sperm, which depending on any given individual clinic's practices requires further processing to be suitable for the needs for IVF, IUI and/or ICSI. This may include further concentration of sperm by centrifugation, counting the sperm concentration and sometimes also determining the motility of the final preparation. It is considered best clinical practice to add a known number of sperm in a known concentration of motile sperm to oocytes. These additional steps add more manual steps to the process, and more sub-samples of the processed sperm to be handled and traced. These concentration counts—and often also the assessments of final motility—are done either manually using hemocytometers or Makler chambers and assessment under microscope, or in laboratories large enough to warrant a separate sperm analysis equipment (computer assisted sperm analysis, CASA), using a CASA instrument such as for example SQA-V Gold by Medical Electronic Systems Global.

Other drawbacks of some known prior art include the following:

Sperm must be removed from the processing vehicle after processing to halt diffusion of components in seminal plasma into buffer solution;

Variability in processing due to multiple human interactions with sample during processing;

No concurrent or linked visual assessment of sperm (concentration, motility, morphology) on current sperm processing platforms;

Separate aliquot of processed sperm for analysis is required

Long processing time exposing sperm unnecessarily long to seminal plasma constituents;

Multiple reagents required;

Multiple consumables required;

Many processing systems subjected to environmental conditions of the laboratory including temperature and ambient atmosphere (either at the bench or in a box incubator).

SUMMARY OF INVENTION

It is an object of the embodiments described herein to overcome or alleviate at least one of the above noted drawbacks of related art systems or to at least provide a useful alternative to related art systems.

In a first aspect of embodiments described herein there is provided a method of processing a semen sample comprising the steps of: introducing the semen sample into a first volume disposed adjacent a second volume comprising buffer solution; wherein the first and second volumes are adapted for fluid communication therebetween; selectively separating the first volume from the second volume with a movable closure member disposed therebetween; wherein the step of selectively separating the first volume from the second volume comprises moving the closure member so that a fluid communication aperture is formed by one or a combination of the closure member or the closure member in combination with the first and second volumes to allow fluid communication between the first volume and the second volume such that motile sperm migrate from the semen sample in the first volume to the buffer solution in the second volume.

Preferably, the dimensions of the fluid communication aperture are proportional to the displacement of the closure member.

The method may further comprise the step of: conducting visual analysis of the sperm that has entered the second volume of buffer solution. Preferably, the visual analysis is conducted concurrently with the sperm entering the second volume.

In another aspect of embodiments described herein there is provided apparatus for processing a semen sample comprising: i) a first well comprising a volume adapted for accommodating the semen sample; ii) a second well comprising a volume adapted for accommodating buffer solution where the first and second wells are adapted for fluid communication therebetween; iii) a movable closure member disposed between the first and second wells for selectively separating the first volume from the second volume; wherein movement of the closure member with respect to the first and second volumes forms a fluid communication aperture allowing fluid communication between the first volume and the second volume such that motile sperm migrate from the semen sample in the first volume to the buffer solution in the second volume.

In the above apparatus, preferably the dimensions of the fluid communication aperture are proportional to the axial displacement of the closure member.

The apparatus may further include a third well comprising a third volume for accommodating progressive sperm.

Furthermore, the apparatus may further comprise an optic path formed in the apparatus comprising a flow path for a thin film of fluid formed between two transparent windows orthogonally disposed to the optical path. A camera may also be disposed in the optic path for conducting visual analysis of the sperm that has entered the second volume of buffer solution.

In yet a further aspect of embodiments described herein there is provided a method of separating a biological component from a biological sample comprising the steps of: introducing the biological sample into a first volume disposed adjacent to a second volume comprising buffer solution; selectively separating the first volume from the second volume with a movable closure member disposed therebetween; wherein the step of selectively separating the first volume from the second volume comprises moving the closure member so that a fluid communication aperture is formed by one or a combination of the closure member or the closure member in combination with the first and second volumes to allow fluid communication between the first volume and the second volume such that the biological component migrates from the biological sample in the first volume to the buffer solution in the second volume.

In the method disclosed above, the dimensions of the fluid communication aperture may be proportional to the displacement of the closure member and, the method may further comprise the step of: conducting visual analysis of the biological component entering the second volume of buffer solution. Preferably, the step of conducting visual analysis is performed concurrently with the biological component entering the second volume of buffer solution.

In still another aspect of embodiments described herein there is provided apparatus for separating a biological component from a biological sample comprising: i) a first well comprising a volume adapted for accommodating the biological sample; ii) a second well comprising a volume adapted for accommodating buffer solution where the first and second wells are disposed adjacent to each other; iii) a movable closure member disposed between the first and second wells for selectively separating the first volume from the second volume; wherein movement of the closure member with respect to the first and second volumes forms a fluid communication aperture allowing fluid communication between the first volume and the second volume such that biological component migrates from the biological sample in the first volume to the buffer solution in the second volume.

In the apparatus disclosed above the movement of the closure member may be axial movement with respect to the first and second volumes disposed coaxially to each other.

Preferred embodiments of the invention include apparatus adapted for processing a semen sample, said apparatus comprising: processor means adapted to operate in accordance with a predetermined instruction set, said apparatus, in conjunction with said instruction set, being adapted to perform the method steps as disclosed herein.

Preferred embodiments of the invention include apparatus adapted for processing a biological component in a biological sample, said apparatus comprising: processor means adapted to operate in accordance with a predetermined instruction set, said apparatus, in conjunction with said instruction set, being adapted to perform the method steps as disclosed herein.

Preferred embodiments of the invention include a computer program product comprising: a computer usable medium having computer readable program code and computer readable system code embodied on said medium for operation within a data processing system and adapted for processing a semen sample, said computer program product comprising: computer readable code within said computer usable medium for performing the method steps as disclosed herein.

Preferred embodiments of the invention include a computer program product comprising: a computer usable medium having computer readable program code and computer readable system code embodied on said medium for operation within a data processing system and adapted for processing a biological component in a biological sample, said computer program product comprising: computer readable code within said computer usable medium for performing the method steps as disclosed herein.

Other aspects and preferred forms are disclosed in the specification and/or defined in the appended claims, forming a part of the description of the invention.

In essence, embodiments of the present invention stem from the realization that providing all motile sperm in a clinically useful sample volume a very short distance to swim before being separated into a buffer volume reduces processing time. Furthermore, the incorporation of a gate to initiate and halt processing with a solid barrier gives a unique method of controlling interface formation without the need for complex closed microchannel networks and accompanying fluid control systems. In addition, there is a realisation that an increase in the ability to concentrate motile sperm during a separation step can be provided by allowing for large semen volume(s) compared to small buffer volumes, or in other words providing a large semen/buffer volume ratio in favour of semen sample, for example with use of a concentric or other equivalent design. Previously, these concentration factors have been overlooked, or dismissed as solvable through centrifugation concentration, with its added steps and possible centrifugation-related consequences. In contrast to the above, current solutions do not address both the volumetric through-put requirements for clinical processing of sperm, and still have long processing times relative to the viable lifespan of motile sperm.

Advantages provided by the present invention comprise the following:

Reduction of work steps required;
Reduction of sample movements from one container to another;
Obviates need for several double witnessing steps during the processing of a sample;
Allows output sperm to be stored in the consumable after processing while maintaining remaining semen sample separate from the processed sperm;
Reduced process duration;
Reduces pre-preparation required before starting the process;
Allows flexibility in the process, for example process duration adjustment based on the number of sperm needed and the purpose it is needed for;

Manual intervention only required at the start (loading) and at the end (removal of sorted sperm);

Operator relieved to do other tasks during the actual processing;

Reduces need for the operator to attend the end of the process in a time-sensitive manner;

Fewer manual steps and handling and reduced process duration mean no separate dedicated work stations for different samples are required;

Reduction in space demands in the laboratory;

Reduction in instrumentation demands in the laboratory as no separate centrifuge(s) or laminar flow hood(s) are required;

Automated processing reduces operator impact on the process;

Automated processing reduces skill levels required form the operators;

Simplified stock control;

Reduced sperm DNA damage, caused by DGC reagents and/or processes such as centrifugation;

Sperm separated from seminal plasma sooner, reducing its exposure to harmful seminal plasma constituents;

Automated sample concentration count removes additional manual step and therefore renders output sperm more suitable and in a faster timeframe for the actual fertilization.

Further scope of applicability of embodiments of the present invention will become apparent from the detailed description given hereinafter. However, it should be understood that the detailed description and specific examples, while indicating preferred embodiments of the invention, are given by way of illustration only, since various changes and modifications within the spirit and scope of the disclosure herein will become apparent to those skilled in the art from this detailed description.

BRIEF DESCRIPTION OF THE DRAWINGS

Further disclosure, objects, advantages and aspects of preferred and other embodiments of the present invention may be better understood by those skilled in the relevant art by reference to the following description of embodiments taken in conjunction with the accompanying drawings, which are given by way of illustration only, and thus are not limitative of the disclosure herein, and in which:

FIG. 3 illustrates the forming of a fluid communication interface in accordance with a preferred embodiment of the present invention;

FIG. 4 illustrates the relationship between vertical translation or movement of a closure member and aperture width of a fluid communication interface in accordance with a preferred embodiment of the present invention;

FIG. 5 shows the formation of a variable aperture in accordance with a preferred embodiment of the present invention;

FIG. 6 represents imaging optics and the formation of a thin film of fluid in accordance with another preferred embodiment of the present invention;

FIGS. 7a and 7b illustrate the loading of a biological sample into a device according to a preferred embodiment of the present invention;

FIGS. 8a and 8b illustrate the loading of a biological buffer solution into a device according to a preferred embodiment of the present invention;

FIGS. 10a and 10b are cross-sectional views of a device in accordance with a preferred embodiment of the present invention;

FIGS. 11a and 11b illustrate the closing actuation of a device in accordance with a preferred embodiment of the present invention;

FIGS. 12a and 12b illustrate the storing functionality of a device in accordance with a preferred embodiment of the present invention;

FIGS. 14a and 14b illustrate the loading of a biological sample into a device according to another embodiment of the present invention;

FIGS. 15a and 15b illustrate the loading of a biological buffer solution into a device according to another embodiment of the present invention;

FIGS. 17a and 17b illustrate the opening actuation of a device in accordance with another embodiment of the present invention;

FIGS. 19a and 19b illustrate the storing functionality of a device in accordance with another embodiment of the present invention;

FIG. 21 is an illustration of another embodiment of a device comprising a deformable spring style element in accordance with a further embodiment of the present invention;

FIG. 27 is an illustration showing respective isometric views of two further embodiments of a device in accordance with the invention;

DETAILED DESCRIPTION

In general terms the present invention addresses the problem of separating motile sperm from a semen sample. In a preferred embodiment of the invention, semen is loaded into a first volume provided by a first fluid well. A sperm buffer solution is loaded into a second volume formed by a second fluid well and a fluid communication interface in the form of an aperture between the wells is opened such that motile sperm can swim through the aperture into the second well. In another preferred embodiment, the present invention provides for the opening of an aperture between a semen sample and buffer solution for active transit of motile sperm into the buffer solution with visual analysis of the sperm entering the buffer chamber through an optic path either concurrently or at any given time point during, before or after the separation process.

Figure 26:
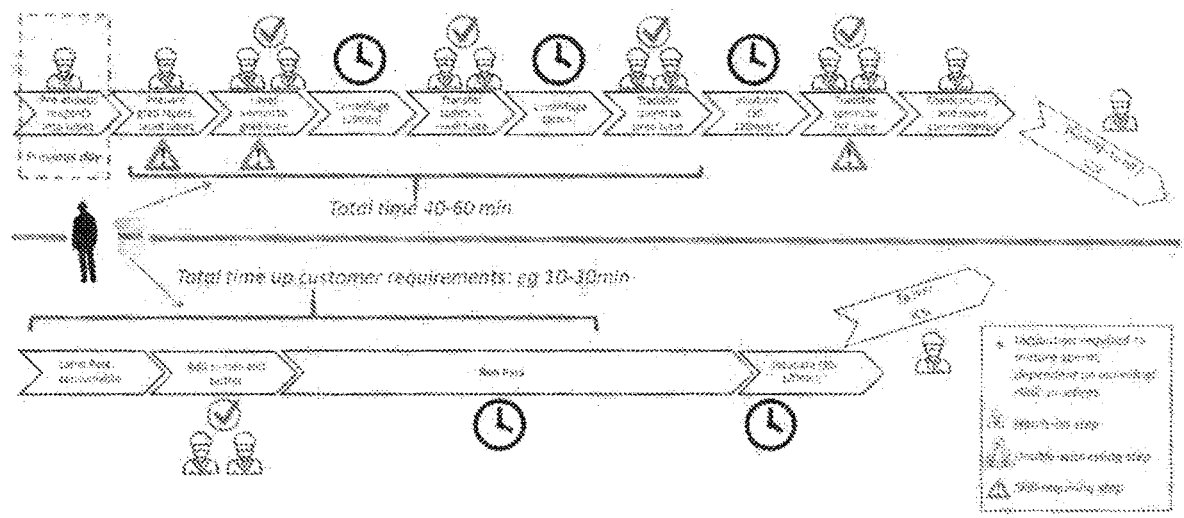
FIG. 26 is a visual comparison between the prior art DGC procedure and exemplary embodiments of the present invention in a procedure labelled as 'Para'.

A general comparison between embodiments of the present invention and the prior art DGC procedure is shown in FIG. 26 showing the advantageous efficiencies of the present invention.

Interface Formation

Opening an aperture is one means of forming a fluid interface between the first and second volumes providing for fluid communication between semen (S) and a sperm buffer solution (B) allowing transit of motile sperm from the semen into the sperm buffer solution. Such an interface is shown in FIG. 3. The aperture A is formed via actuation of at least two interlocking components 1 and 2 between a sealed/closed state (shown at the left-hand side of FIG. 3) separating the two respective fluid wells 3 and 4 open to atmosphere and an open state (shown at the right-hand side of FIG. 3) creating a fluid interface I between the fluids. With reference to FIG. 4, the sealing faces 1a and 2a of the upper and lower components 1 and 2 are substantially parallel and angled θ such that the distance $Y_2$ between the faces 1a and 2a is proportional to the vertical separation $Y_1$ and is determined as a function of that angle θ.

Open System

In preferred embodiments both fluid volumes of the first and second wells 3, 4 respectively are open to atmosphere and are filled to a level such that no pressure head is present when the aperture A is opened and therefore no net fluid transport occurs between the fluid volumes. The dimensions of the interface I or width of the aperture $A_w$ allows for connecting of the fluid volumes with only diffusion-based mixing of the two fluids.

Variable Aperture

With reference to FIG. 5, the aperture width $A_w$ can be varied to control the fluid interface I area, impacting the rate of passage of sperm, and the rate of diffusion of molecules in seminal plasma, over a given time period. This allows separation of sperm based on its motility. Progressively motile sperm will swim to all directions including that of the aperture A. In this respect, it is to be noted that sperm separation will not necessarily be dependent on known edge-trailing effects. Although the most critical factor is sperm motility and its ability to move across from one fluid to another on its own power, sperm with grossly abnormal morphology (for example clearly enlarged sperm head or multiple heads, missing tail or multiple tails) and agglutinated sperm (sperm adhered to each other or to mucus strands, non-sperm cells or debris in non-specific or specific manner) may be prevented to enter the buffer solution B. This allows separating of sperm based on morphological characteristics that influence size, depending on the initial sample types and output required for subsequent ART processing.

The control of the variable fluid communication interface I relies in part on the reversible actuation of components 1, 2 between a sealed state separating two fluid volumes and open state creating the aperture A which provides a static thin fluid interface between the fluids.

A first aspect of embodiments provides a fluid interface I by allowing the controlled opening of a variable aperture A (alternatively a weir, gate, or opening) connecting two static volumes of fluid S, B. The width of the aperture $A_w$ allows for connecting of the fluid volumes without significant mixing of the two fluids S, B. The aperture A is formed by lifting an upper component 1 with features forming one half/side of the aperture A with respect to a lower component 2 with features forming the other half/side of the aperture A.

Variable Sample Volumes

The preferred embodiments of the invention allow for variable volumes of semen, when a matching volume to sperm buffer or media is added to the two fluid volumes.

Storage Within the Device

The variable aperture A can be readily closed without effect on either volume S, B once a sufficient quantity has been separated allowing for temporary storage prior to using the sample in subsequent ART procedures and halting further passage of sperm and diffusion of seminal plasma constituents.

Optical Detection of the Samples

With reference to FIG. 6, a section of the separated fluid volume is present as a thin film of fluid suitable for cell imaging techniques. A camera C in an optic path allows for capture and direct image analysis of the separated sperm properties including, for example, concentration, motility, and morphology. The analysis can be done at any time point during motile sperm separation or at the end the separation protocol. The thin film is created between the planes of two flat surfaces $F_1$ and $F_2$. The gap between these planes is adjustable and may be actuated in conjunction with or independently of the interface I (gate) between the two fluids. Alternatively, other analysis solutions may be provided. For example, a separable portion of the sample processing apparatus (for instance a portion of the second well or a lid portion of the apparatus) which may also be a removable part containing the processed sample may be removed and placed within an optical path of an instrument for image capture.

A second aspect of embodiments provides visual assessment of the sperm through an optical viewing window in the buffer containing volume of the device. Motile sperm that swim through the aperture A from the semen sample S can be visually assessed by image analysis of sperm movements captured by video microscopy. It is to be appreciated that image analysis techniques utilising available software algorithms may be employed to conduct appropriate visual assessment of the processed sample, as would be appreciated by the person skilled in the art. In this respect, in one preferred embodiment, a typical laboratory instrument comprising any of the variations of the device 10 as illustrated in FIGS. 7 to 25 and the optical instrumentation as exemplified schematically in FIG. 6 would be configured to allow the sample container to be sorted and imaged via the optics module simultaneously. Another embodiment would be configured to allow the automatic transfer of the sample container from sorting location to optical detection system to allow imaging of the sample.

The instrument's optical system may automatically adjust the focus of the camera via an electro-mechanical control device. Another embodiment of this feature would be to take a number of images at varying height increments throughout the optics thin film chamber in the device, with an algorithm that detects the most focused image for detection and analysis.

The accompanying laboratory instrument may also be configured to allow optical detection and analysis of raw or processed semen samples in the sorting device 10 or, alternatively, on a variety of standard microscope slides. This provides for a variety of laboratory workflows by allowing sperm counts to be completed on standard slides at initial semen analysis or after extended incubation in an existing laboratory incubator.

Sample Result Visualisation and Identification

The accompanying laboratory instrument will also be adapted to display the result, or state of progress for each test to aid operator time management. The visualisation of the progress of the sorting may be by displaying either a sperm sorting time remaining until result, or percentage of sperm count complete, or motility of the sperm collected so far or some other indicative method. The display may also feature video or image feed at certain sections of the workflow, for example of the raw sample before processing and the sample collected so far. Logging of these images, videos or displayed results may be possible via instrument network access. Furthermore, the instrument may include a barcode scanner to allow the patient's ID, operator ID, and sample ID to be logged and tracked along with images and results.

Multiple Separation Volumes for Motility Based Grading

A third fluid volume may be separated from the second volume by the or another fluid communication interface in the form of a second closure member to allow further separation of motile sperm present in the second volume. Fast-progressive sperm from a mixture of slow and fast progressive sperm can move into this third volume when the closure structure is opened through the formed aperture. Sperm of highest motility can move through both apertures into the third fluid volume, such that the ratio of fast progressive to slow progressive sperm in the third volume is greater than that in the second volume. A further fluid volume will also allow for any need of a middle volume between semen and buffer to better control fluid movements. As an alternate embodiment, it is envisaged that a modification to the sample processing apparatus may include three volumes where semen is in the middle and buffer on both sides, to make the separation of processed sample even faster.

The instrument may include automated sample separation where one volume of fluid is removed from the chamber and placed in a separate vessel for further processing. The sample may be removed by a pipette system, fluidic tubing system attached to the chamber, 'dip stick' plunged into the sample within the chamber or other such means.

The instrument may include multiple processing and imaging modules to simultaneously process multiple samples concurrently. The instrument may have a chamber transfer system, where the chambers are taken from the storage area, placed on the actuation and analysis module and then removed for further processing.

A third aspect of embodiments allows for the closure of said aperture separating the semen sample from the buffer solution now containing a portion of the motile sperm originally present in the semen sample volume.

Additional refinements may be included in preferred embodiments where:

Surfaces are treated to reduce binding of sperm to the base polymer;

Surface textures or structures are provided that rectify the direction sperm swim in the direction of the aperture.

The complexity of processing a biological sample such as semen to remove seminal plasma and extract the motile sperm component is now able to be performed in a single consumable and automated requiring only 1× sample input and 1× sample removal. This reduces work steps required.

Movement of sperm through several containers, exposing sperm to damage, mishap and contamination may be avoided in embodiments of the invention utilising a single consumable where sperm stays from the start to the end of the process. This reduces sperm movements. With the use of the single consumable of preferred embodiments where sperm stays from the start to the end of the sorting process there is no need to double witness the sperm movement at every point when it is moved from one container to another.

The consumable design of preferred embodiments allows fast recovery of motile sperm, the number of collected sperm being able to be adjusted by controlling the duration of the process and/or the starting volume of the sample. The process duration is short, and can be adjusted based on the number of sperm needed.

With reference to FIGS. 7 to 13 of the drawings a first exemplary embodiment is described.

A device 10 providing a fluid communication interface in the form of a toothed gate is provided (best depicted in vertical cross section by FIGS. 10a and 10b) as a closure member between sample volume S and buffer volume B. The aperture A' opens upon rotation of a cam ring 6 that lifts the closure member on this action. Apertures A' open to form a fluid interface and allow fluid communication between the teeth 7 at a ratio of the vertical travel to aperture width $A'_w$.

In a preferred embodiment, the vertical apertures A' may open between the teeth 7 at a 1:10 ratio of vertical travel of the upper part 8. In this embodiment, sperm can swim along multiple trajectories through apertures A' into the buffer B.

Semen is loaded, in a quantity for example of ~1 mL, by use of a pipette PS into the first fluid volume 4 of the device, which may be situated as an outer ring as shown in FIGS. 7a and 7b. At the step of loading, the device 10 is in the closed state with a seal formed between the teeth 7 of the upper 8 and lower 9 parts.

Whilst in the closed state, sperm buffer B is loaded, again by use of a pipette PB, into an inner ring volume of the device 10.

The fill levels must be the same or slightly higher in the buffer level to avoid flow of neat semen into the inner sorting volume 3.

Figure 1:
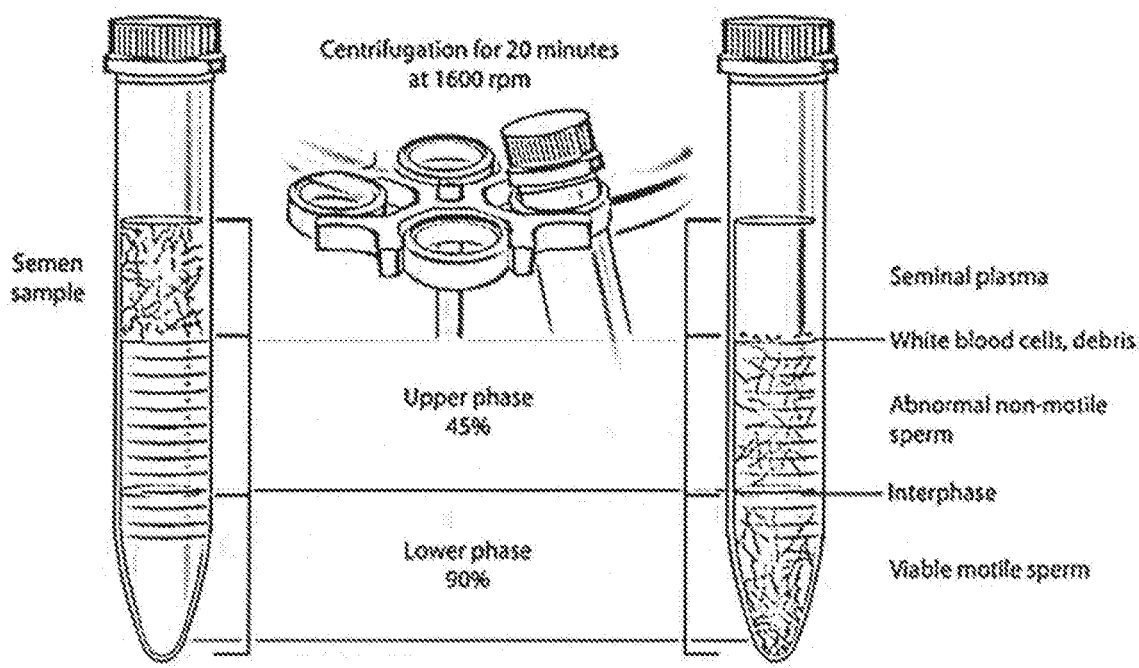
FIG. 1 illustrates the prior art sperm processing methods of density gradient centrifugation (DGC)
Figure 2:
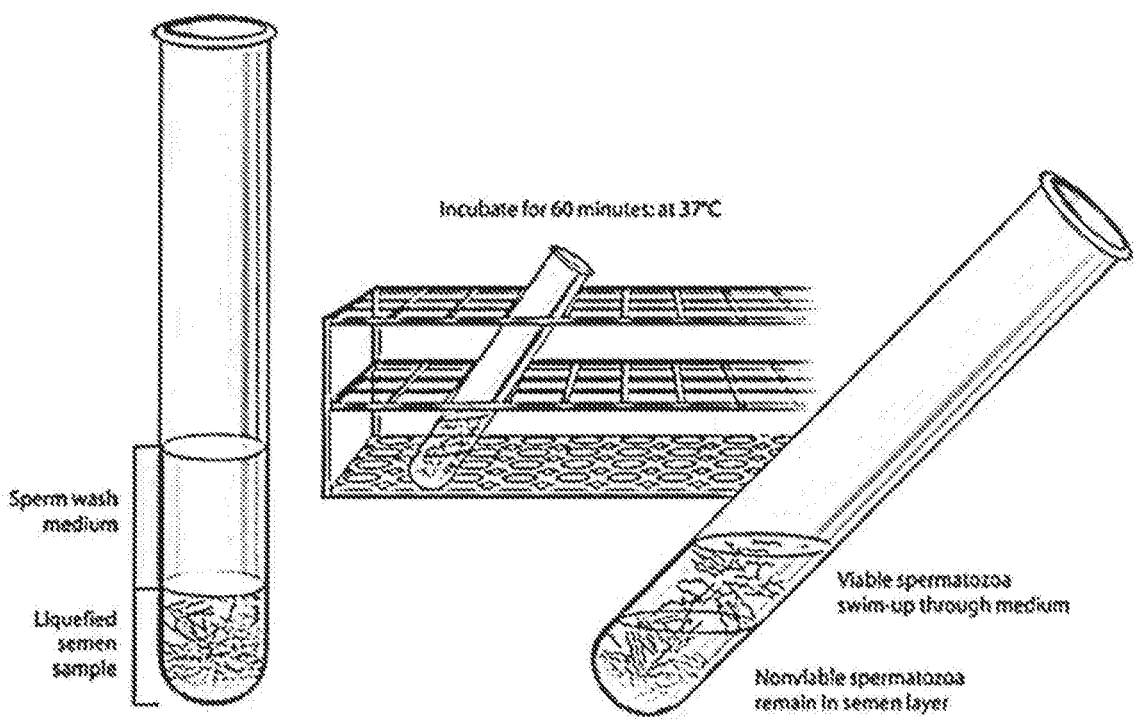
FIG. 2 illustrates the prior art "swim up" sperm processing method.
Figure 9B:
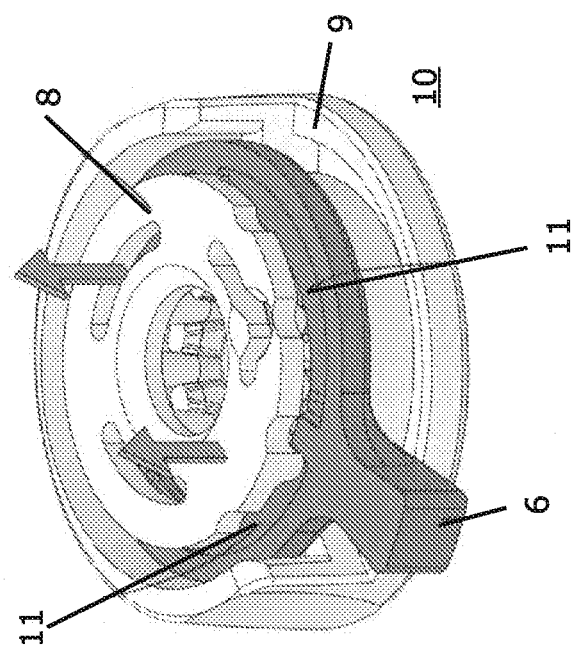
FIGS. 9a and 9b illustrate the opening actuation of a device in accordance with a preferred embodiment of the present invention.
Figure 9A:
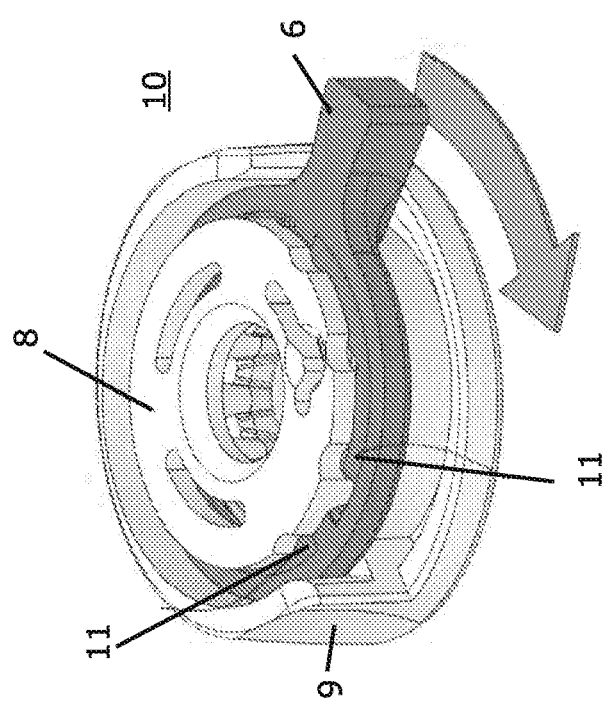

A fissure is created between the two fluid volumes when the cam ring 6 is rotated, as shown in FIGS. 9a and 9b. Upon this rotation of cam ring 6, the upper part 8 is pushed or displaced upwards by ramps 11 disposed on the cam ring 6. Equally, the illustrations of FIGS. 11a and 11b show the closure mechanism of the device 10 by reversal of the rotation of the cam ring 6.

The top cross-section view of FIG. 10a shows sperm in the outer-ring volume 4 and sperm swimming into the inner volume 3 is shown in FIG. 10b after actuation of the cam ring 6 opening a vertical aperture A' between the two fluids.

If required, teeth 7 can be closed preventing diffusions of seminal plasma and further sperm into the sperm buffer volume 3 prior to aspiration of the sorted sperm S. Motile sperm can be aspirated with a pipette from the inner volume. The cross-sectional view of FIG. 12b shows this closure state with sperm in the inner volume 3 prior to aspiration.

Figure 13:
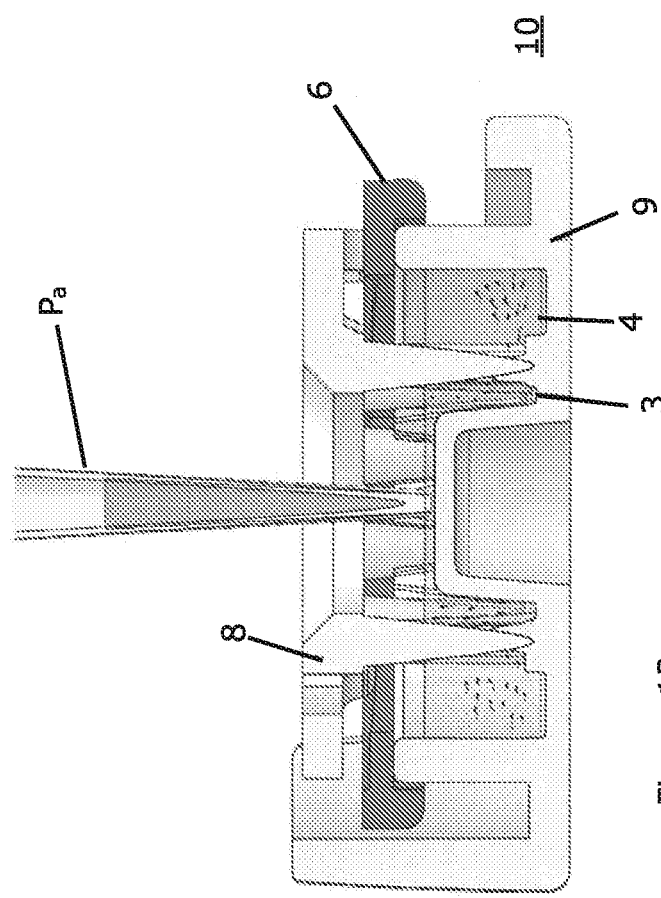
FIG. 13 shows an aspirating of buffer solution containing biological sample in accordance with a preferred embodiment of the present invention.

FIG. 13 shows the step of motile sperm being aspirated with use of a pipette Pa from the inner volume 3.

With reference to the FIGS. 14 to 20 a second exemplary embodiment is described, which is a mechanical variation to the first embodiment depicted in FIGS. 7 to 13.

The device 10 comprises a base component 9 and closure member 8, 6 comprising a cylindrical wall separating the fluid volumes with a sealing face at the base the cylinder that mates to the base component 9. In the closed state a seal is formed between the base component 9 and closure member 8. Semen sample S may be loaded into the first fluid volume 4 of the device. Sperm buffer B may also be loaded into second fluid volume 3 of the device. The fill levels must be the same or slightly higher in the buffer volume to ensure no active flow of neat semen into the buffer sorting volume opening the closure member.

As shown in FIGS. 14a and 14b, semen is loaded into the outside volume 4 of the device 10 in much the same manner as the previous embodiment using a pipette PS. The device 10 is in the closed state with a seal between the base component 9 and cylindrical top piece 8.

As shown in FIGS. 15a and 15b, sperm buffer B is loaded into the inside ring volume 3 of the device 10 using pipette PB. The device 10 remains in the closed state with a seal between the teeth 7 of the upper and lower parts 8,9. The fill levels must be the same or slightly higher in the buffer level to avoid flow of neat semen into the inner sorting volume 3.

Figure 16A:
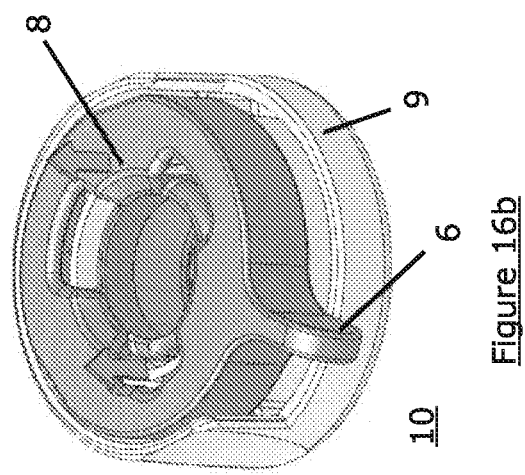
FIGS. 16a and 16b illustrate the opening actuation of a device in accordance with another embodiment of the present invention.
Figure 16B:
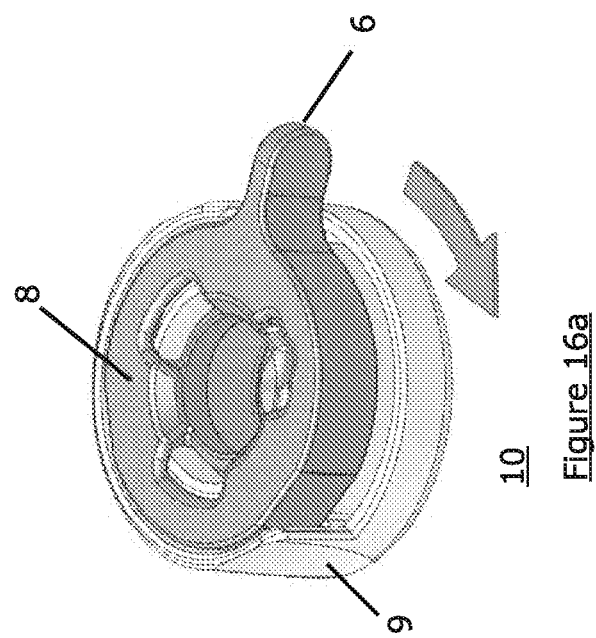

Again, rotation of the cam ring 6, as shown in FIGS. 16a and 16b allows for the opening of an aperture A' between the inner volume 3 and the outer volume 4.

Side cross-section views of FIG. 17a shows sperm located in outer-ring volume 4 and in FIG. 17b sperm is shown swimming into the inner volume 3 after actuation of the cam ring opening the annular aperture A' between the two fluids.

The closure member 8 can be actuated back to a sealed state to halt both migration of motile sperm across the interface and diffusion of seminal plasma into the sperm buffer volume 3. Sorted motile sperm can be held in the second fluid volume 3 until they are aspirated from the device 10.

Figure 18B:
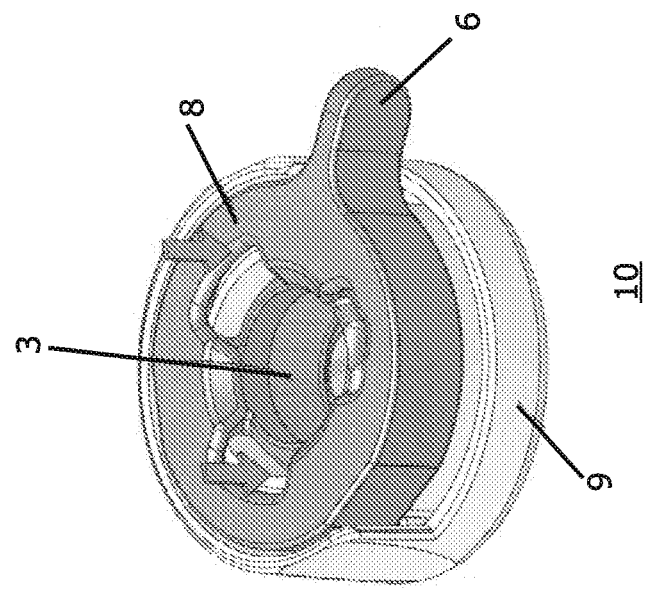
FIGS. 18a and 18b illustrate the closing actuation of a device in accordance with another embodiment of the present invention.
Figure 18A:
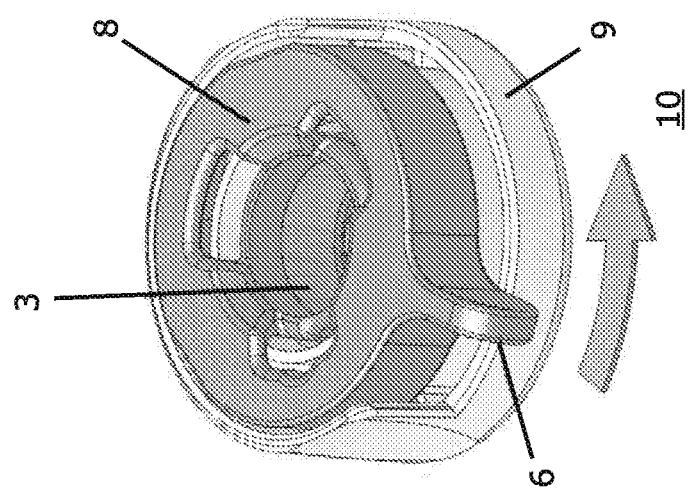
Figure 20:
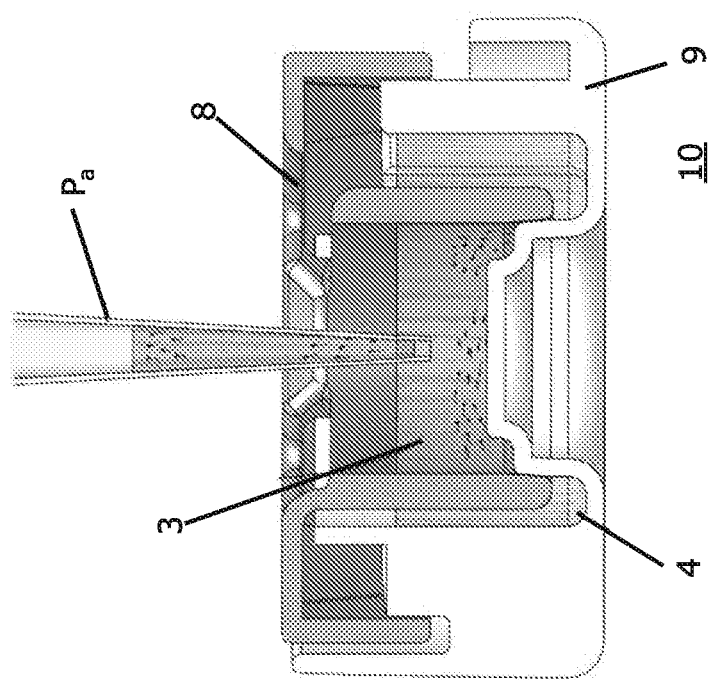
FIG. 20 shows an aspirating of buffer solution containing biological sample in accordance with another embodiment of the present invention.

Alternatively, if required, teeth 7 can be closed preventing diffusions of seminal plasma into the sperm buffer volume prior to aspiration of the sorted sperm. The reversal of the rotation of cam ring 6 as shown in FIGS. 18a and 18b depicts this. FIGS. 19a and 19b show the device holding sperm in a closed state prior to aspiration. Motile sperm can be aspirated with a pipette Pa from the inner volume 3 as shown in FIG. 20.

Alternative Embodiments

As described above and referring to FIGS. 3 to 20, embodiments of the present invention rely in part on the reversible actuation of components between a sealed state separating two fluid volumes and an open state creating a static thin fluid interface between the fluids. On this basis, the following further embodiments have been contemplated.

Forming an Interface

Noting that embodiments of the invention rely on the reversible actuation of components to form a fluid communication interface and in that interface, according to preferred embodiments, an aperture is formed between a sealed state separating two fluid volumes and an open state creating the fluid interface between the fluids. The various embodiments described in the following have been considered and in which that function is provided.

A closure member that separates the first and second fluid volumes may comprise a deformable element. In a compressed state an aperture in the deformable element may be collapsed to form a seal between the fluid volumes. Stretching of the deformable element can open the aperture in the deformable element to a controlled size allowing fluid communication between the fluid volumes 3 and 4. The deformable element may comprise one or a combination of springs, tubes. In certain embodiments, it is envisaged that the element may comprise an elastic formation.

FIG. 21 shows a helical coil 12 (or spring) disposed in a fluid holding dish where two separate fluid volumes 3, 4 are defined, one volume 3 on the inside and one volume 4 on the outside of the coil 12. In a compressed state a seal is formed between the mating surfaces of each turn of the coil 12. Stretching of the coil 12 opens a controlled gap or aperture A" between the coil's 12 turns allowing fluid contact between the fluid volumes 3 and 4.

Figure 22:
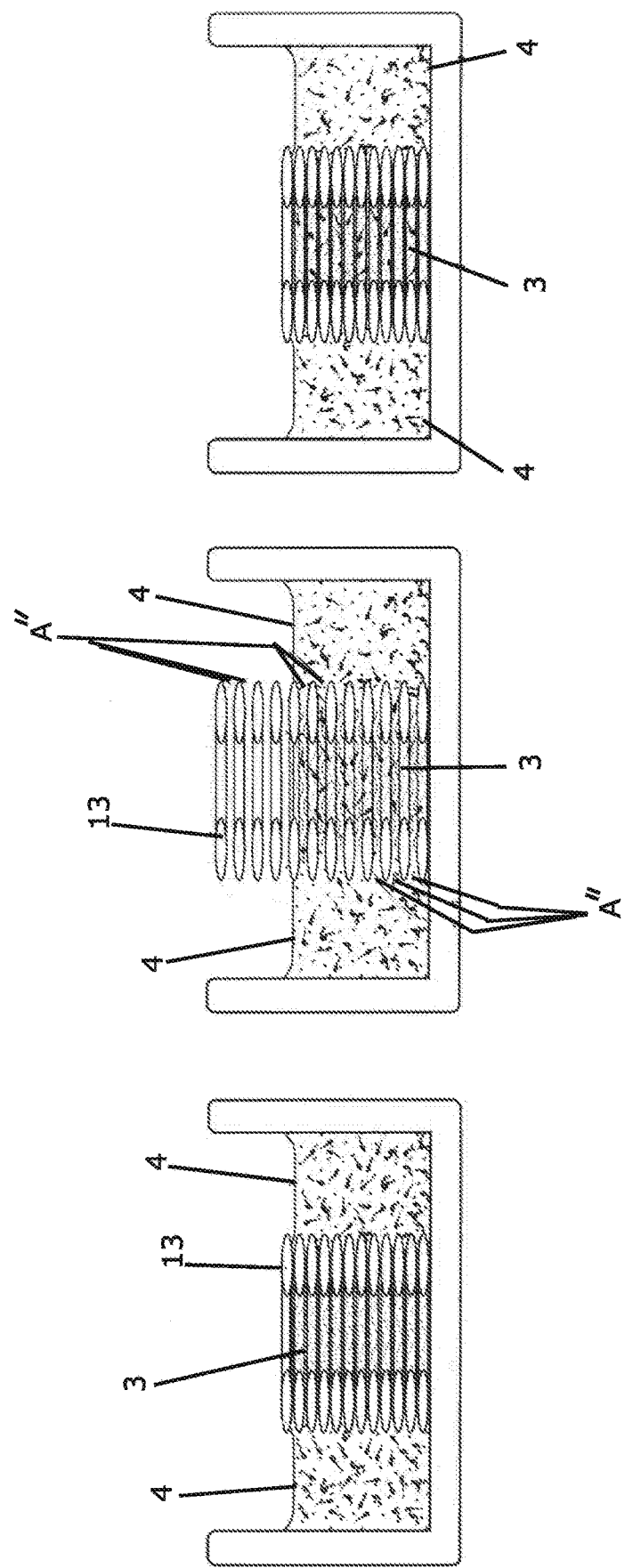
FIG. 22 is an illustration of another embodiment of a device comprising stacked elements in accordance with a further embodiment of the present invention.

FIG. 22 shows stacked formations 13 comprising one or a combination of coils, rings, discs and washers, which are forming a wall where the fluid volumes 3 and 4 are again defined on the inside and outside of the stacked formations 13. Using coils as an example, in a compressed state a seal is formed between the mating surfaces of each turn of the coil 13. The formations 13 are lifted vertically with respect to one another opening gaps or apertures A" between the rings allowing fluid contact between the fluid volumes 3 and 4.

In a general form, not shown, a cylinder forms a wall where the fluid volumes are defined on the inside and outside of the cylinder. The cylinder forms a radial or face seal with a mating surface in the two components. Vertical lifting of the cylinder opens a gap between mating faces allowing fluid contact between the fluid volume.

Figure 23:
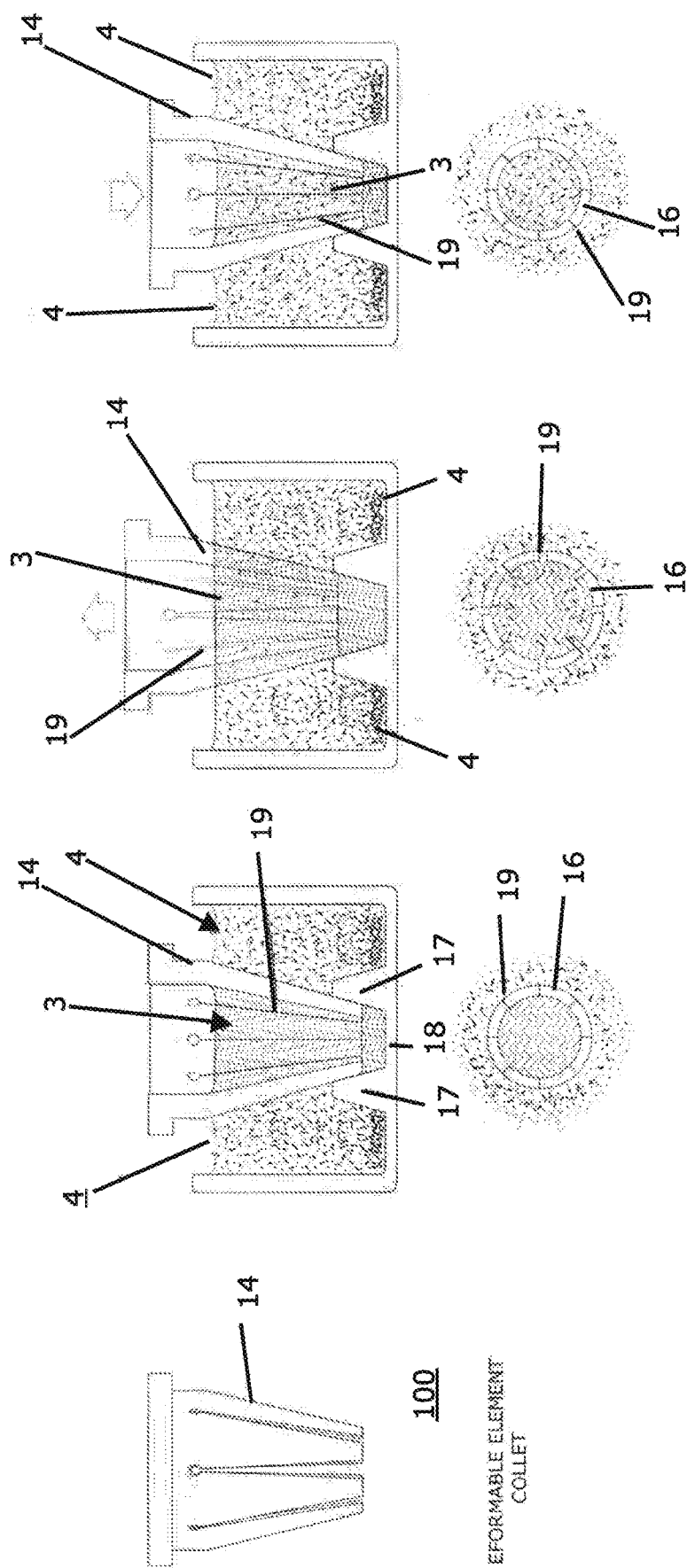
FIG. 23 is an illustration of another embodiment of a device comprising a deformable collet style element in accordance with a further embodiment of the present invention.

FIG. 23 shows a collet structure 100 whereby the slotted tapered cylindrical body 14 forms a wall 16 where fluid volumes 3 and 4 are defined on the inside and outside of the collet, respectively. A mating tapered sleeve 17 and closer structure 18 acts on the collet to form a seal between surfaces of each slot 19 and a radial seal is formed at the intersection with the closure structure 18.

Figure 24:
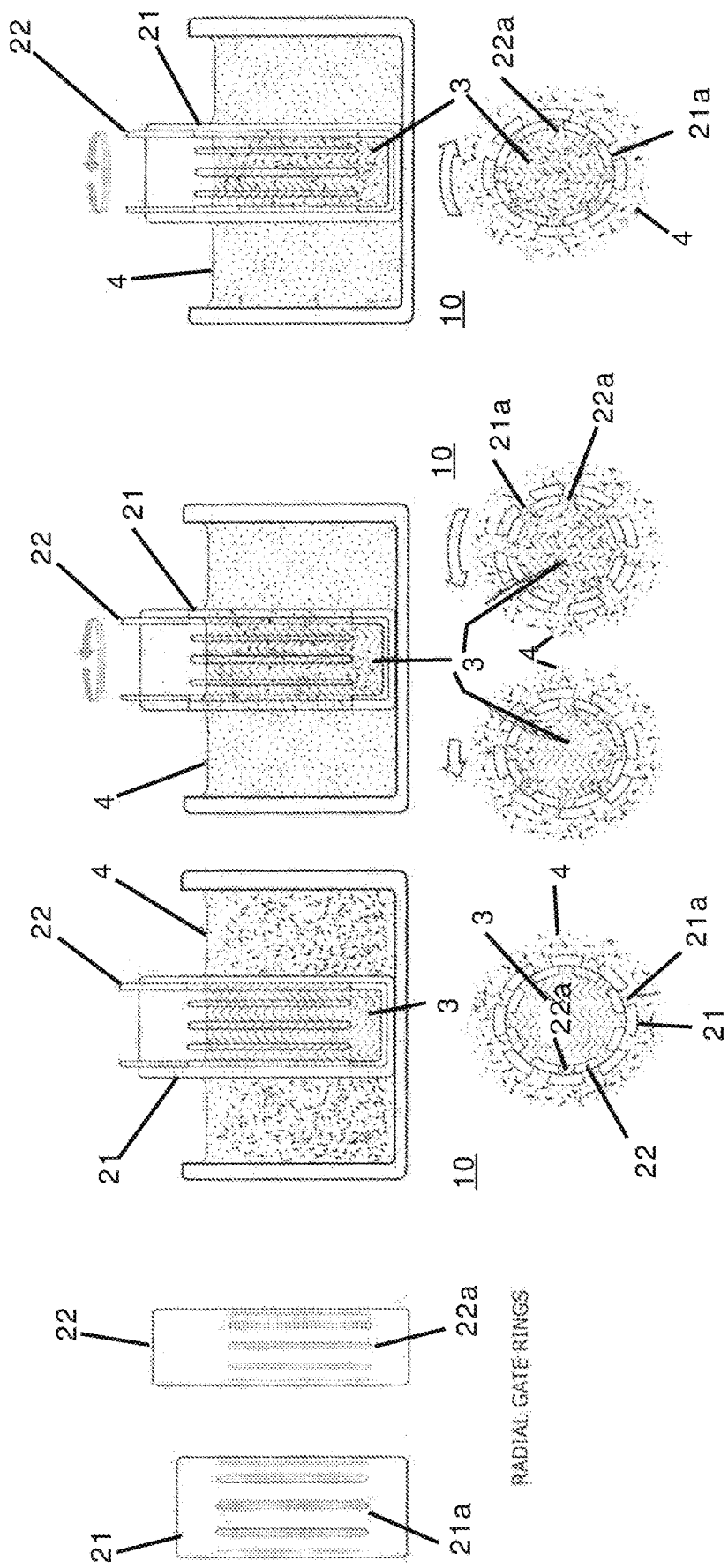
FIG. 24 is an illustration of another embodiment of a device comprising slotted wall elements in accordance with a further embodiment of the present invention.

The embodiment of FIG. 24 shows double slotted walls that separate two fluid volumes where one wall can be moved with respect to the other. A first wall is present on the base component. The second wall is present on a second closure member. FIG. 24 shows two-fluid volumes 3 and 4 are separated by slotted walls 21 and 22 where one wall can be moved with respect to the other. The walls 21, 22 are adjacent and can be moved between a closed state where the slots 21a, 22a in each wall 21, 22 do not overlap, and the open state where the slots 21a, 22a do overlap allowing contact between the fluid volumes 3 and 4. The degree of overlap between the slots will determine the aperture size or width. This embodiment can be configured as two adjacent slotted plates or two slotted cylinders, as shown in FIG. 24.

Figure 25:
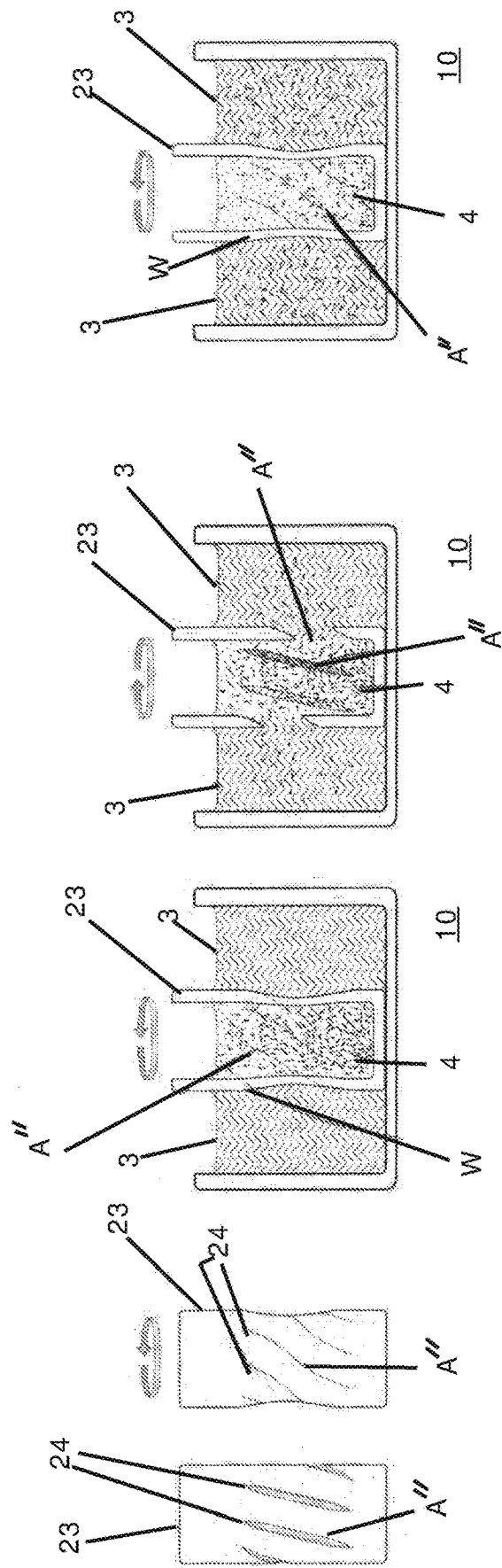
FIG. 25 is an illustration of another embodiment of a device comprising a deformable element in the form of a flexible tube in accordance with a further embodiment of the present invention.

In FIG. 25 an aperture formation A" is shown where a wall W is formed between two fluid volumes 3 and 4, respectively. The wall comprises a flexible cylinder 23 containing slits 24 that upon distortion of the cylinder 23 the slits 24 open to a variable degree forming an aperture A" between the two fluids, S and B of volumes 4 and 3, respectively.

Actuation

Actuation of the aperture of the fluid communication interface can be effected by way of automated instrumentation, as would be appreciated by the person skilled in the art. For example, the aperture opening movement may be performed by action of an electro-mechanical actuator of the instrument (such as a stepper motor or piezo-electric motor) onto the closure member of the device. The aperture may be operated so that it opens and closes by actuation of a cam whereby a cam follower is integrated on the device. The actuator is a component of the instrumentation of the laboratory that interconnects with the device 10. Alternatively, the actuator may be a component of the consumable assembly of the device 10.

Automated actuation of the fluid depth in the optics window can be effected by the optics window containment surface opening by action of an electro-mechanical actuator in the instrument (such as a stepper motor or piezo-electric motor) onto the closure member of the device. The optics window containment surface may be operated so that it opens and closes by actuation of a cam whereby a cam follower is integrated on the device. The actuator is a component of the instrumentation of the laboratory that interconnects with the device 10. Alternatively, the actuator may be a component of the consumable assembly of the device 10.

Temperature Control and Logging

The accompanying laboratory instrument may contain an incubation chamber(s) to allow the setting and control of incubator temperature anywhere from ambient to 40 deg C. The temperature and humidity of the incubation chamber(s) may be recorded and logged as part of the results output, or displayed on the accompanying user interface.

Another embodiment may allow the devices to be stored in the incubation chamber for a period of time either before or after processing for pre-heating or post-incubation.

Sample Thawing

The incubator module of the accompanying laboratory instrument may allow samples to be thawed by providing features to locate commonly used semen storage straws. The instrument may introduce agitation on demand to aid the thawing of samples. The agitation would be controlled during a thawing protocol via controlled electro-mechanical vibration.

Instrument Configuration

The accompanying instrument may consist of either a single sorting/incubation/analysis chamber, or multiples of the aforementioned modules to assist with laboratory scheduling and workflow. These instruments may be modular to allow connection to existing instruments, or stand alone to accommodate to smaller clinical environments.

The instrument may consist of either a single optics detection module, or multiple detection modules, independent of how many sorting or incubation modules exist. The configuration may be adapted depending on resulting analysis of the market and existing scheduling and workflows used in the industry.

Smart CASA

The accompanying laboratory instrument may be able to reduce time taken to sort motile sperm by enabling a Smart CASA (Computer-Assisted Sperm Analysis) algorithm, which may read motility and concentration of the collected sample in real time while it is being processed, thus allowing the user to terminate the sorting when a sufficient amount of sufficiently motile sperm has been collected. This would allow adjusting the duration of the test to respond to specific sperm sorting needs and clinical situations.

Modifications and Enhancements

Any of the above described embodiments can be enhanced by inclusion of one or more of the following modifications or enhancements:
  Surfaces treatments, such as inclusion of blocking agents (e.g. human serum albumin) to reduce non-specific binding of sperm to the base polymer
  Surfaces of the fluid volumes treated to promote specific binding of non-progressive, abnormal sperm or non-viable sperm
  Specific medium containing, for example, immunobeads binding certain sperm. Alternatively, beads may be added to semen or biological samples at the time of loading. One or a combination of these modifications may be employed to work in concert together
  Surface textures, structures or protrusions that rectify the direction sperm swim or otherwise limit the degrees of freedom of the sperms movement such that a greater proportion of motile sperm move in the direction of the aperture or inhibit movement from the buffer volume back toward the sample volume
  Chemical concentration gradients between the buffer and sample volumes such that sperm are induced to swim toward the buffer volume (i.e. chemotaxis)

Solid phases or surfaces for temporary binding and release of sperm

Figure 28:
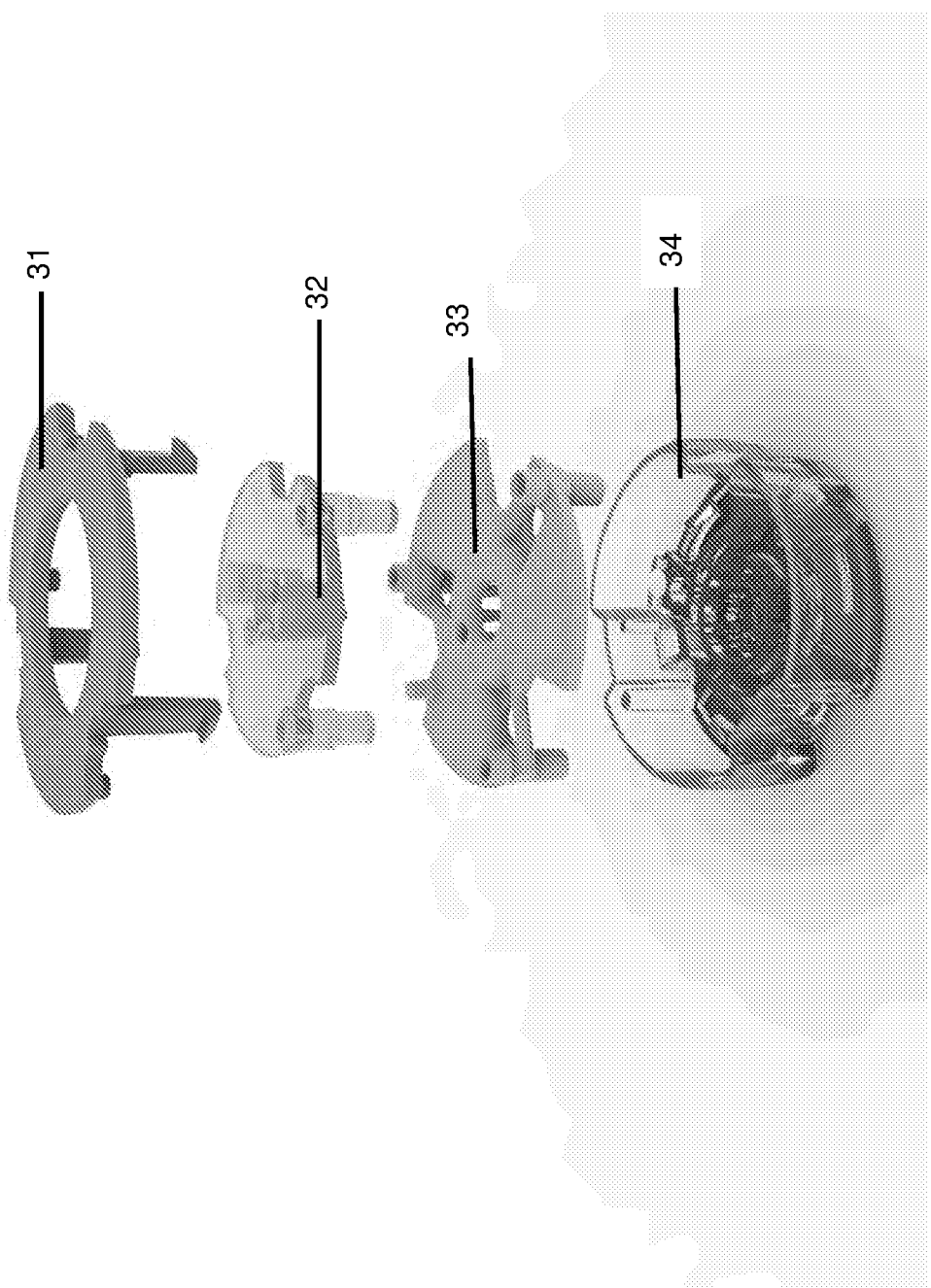
FIG. 28 is an exploded view of one of the embodiments of FIG. 27 showing its components.

With respect to FIGS. 27 to 31, a prototype embodiment of the invention is described. A consumable device 10 is illustrated in two prototypical forms in FIG. 27 with like reference numerals used for the same components as described above. In FIG. 28, an exploded vertical view of one of the devices 10 of FIG. 27 is illustrated showing, firstly, a clip-on cap 31 that allows easy assembly of springs. A lid 32 with base part creates a restricted space in use to form a thin film of fluid for imaging. The lid also includes ports for sample input/output. A gate 33 is included with flanged features to create the top half 8 of the device. Finally, a base 34 is included with bottom gate/chamber features and clips to retain the consumable in the instrument.

Figure 30:
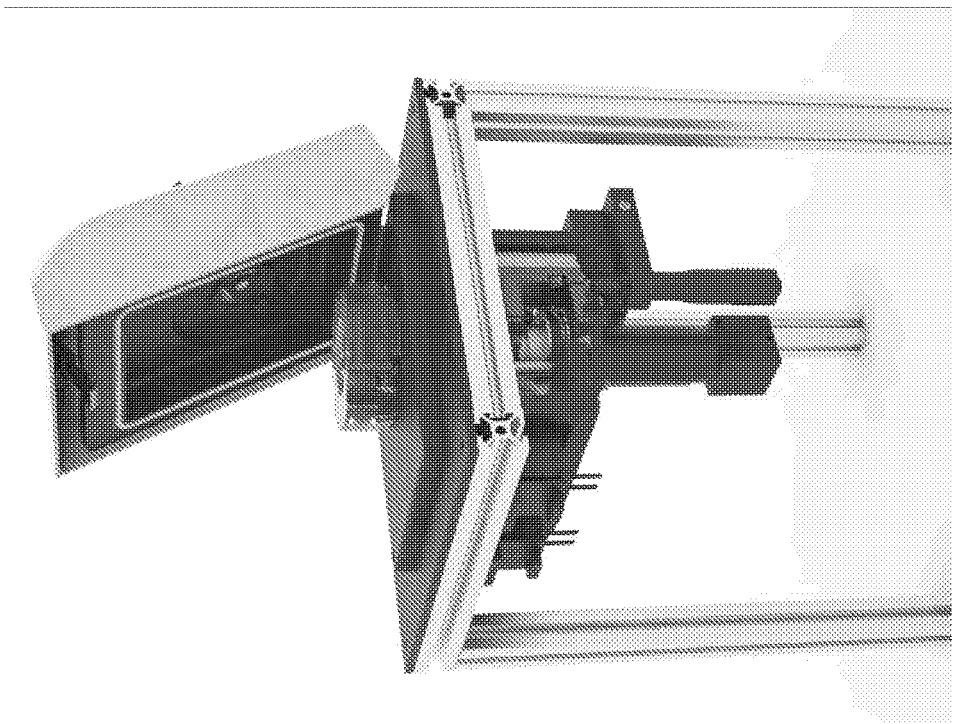
FIG. 30 is an illustration of the instrument of FIG. 29 with its cover open.
Figure 29:
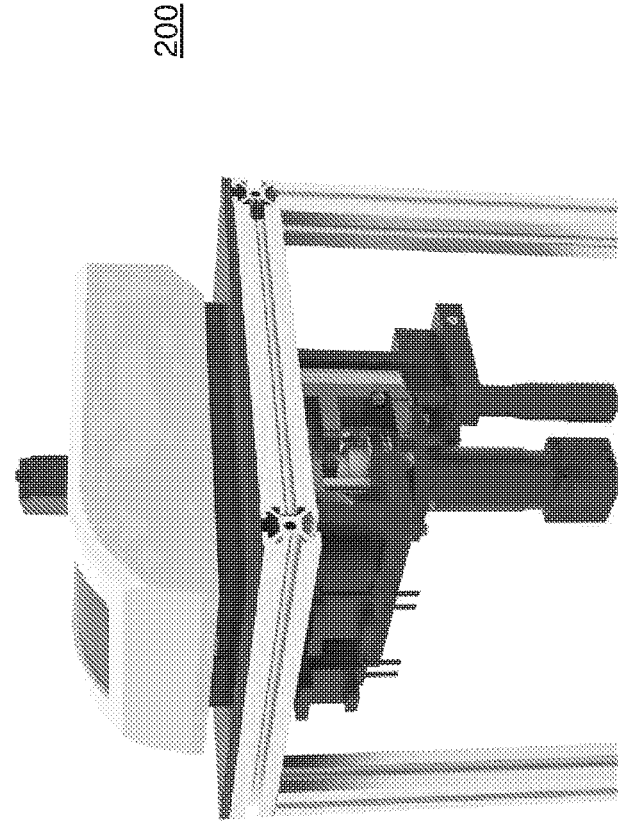
FIG. 29 is an illustration of a laboratory instrument adapted for incorporating the sample device in accordance with an embodiment of the invention and showing a closed cover of the instrument.

FIGS. 29 and 30 show partial cut-away perspective views of a prototypical instrument 200 for housing and operative control of, inter alia, the consumable device 10 and an optical detection unit. FIG. 29 shows the instrument in a closed cover disposition and FIG. 30 shows the instrument with its cover open.

Figure 31:
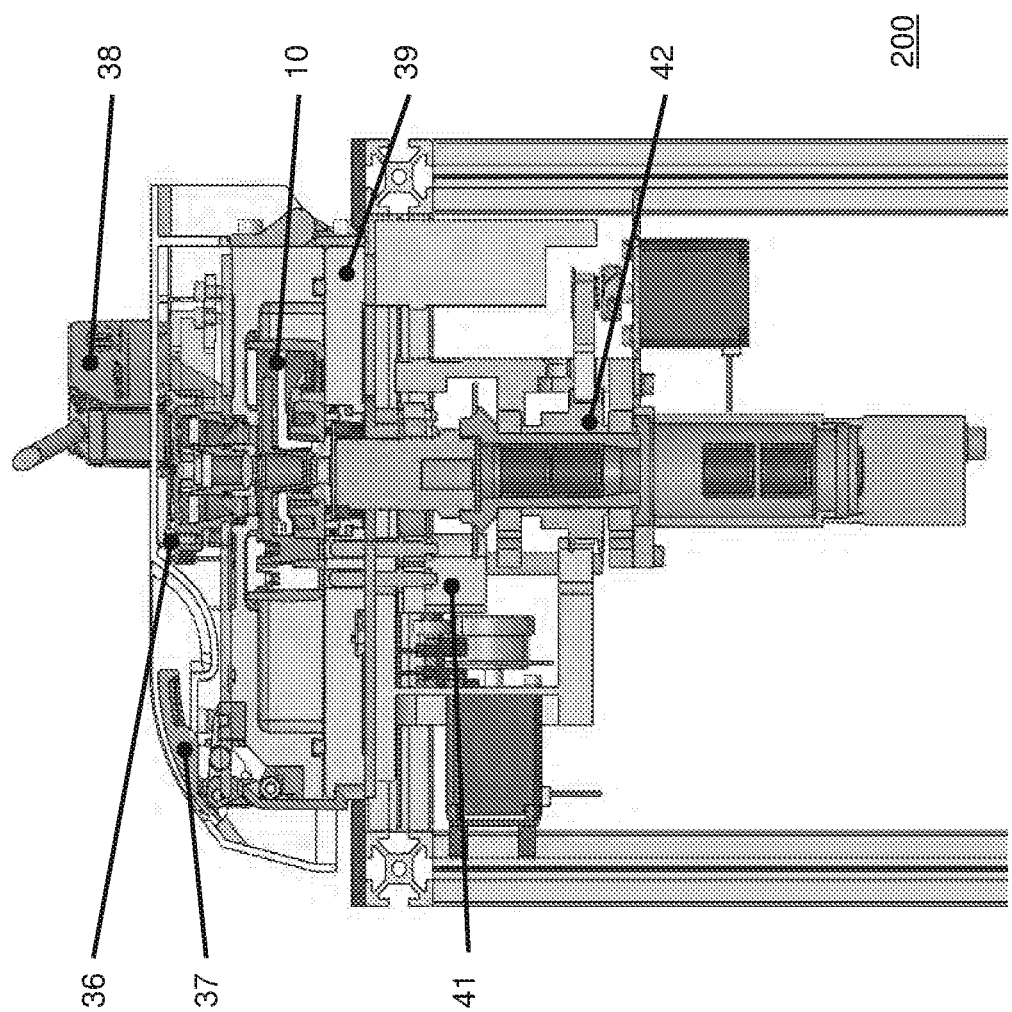
FIG. 31 is a further illustration of the instrument of FIGS. 30 and 31 in side view showing its components.

FIG. 31 shows a side cut away view of the instrument 200 illustrating some of its operating elements and components. Access to the instrument for samples is provided by reusable latch 37. A dark field lighting unit 36 is situated at the top portion of the instrument. Laser distance sensor 38 allows for consumable gate aperture measurement. The consumable device 10 is integrated as shown into the instrument. Hinged incubator 39 is designed with variable set temperature. The actuator 41 provides for automated consumable actuation which allows variable gate set size. An image sensor with optics rotation system 42 is also integrated into the instrument 200.

Experimental Results

1. Introduction and Aims

Large numbers of tests were performed during the development of the consumable designs of preferred embodiments, including those described above, to test their performance, as well as after increased design iterations. The results presented here represent a subset of those tests, conducted with two preferred design revisions.

The main objectives of the tests were to test performance of consumable prototypes in regards to the ability to sort the (progressively) motile sperm from raw semen sample. The tests concentrated in key parameters such as total sperm concentration, sperm progressive motility, and concentration of progressively motile sperm in the final washed sample (output). In addition, timing of the sorting was assessed by repeated sampling over an extended time period.

The secondary objective of the tests was to capture comparison data between two particular design prototypes in order to assist in the selection of most promising consumable iteration.

The tertiary objective of the tests was to assess fluidics of the devices in regards to leakages of buffer and/or semen between compartments or volumes during sorting and at the end of the sorting run.

2. Definitions
Total sperm motility: Proportion of all sperm showing motility, whether progressive or non-progressive.
Progressively motility: Sperm moving actively, either linearly or in a large circle, regardless of speed.
Non-progressively motility: All other patterns of motility with an absence of progression, e.g. swimming in small circles, the flagellar force hardly displacing the head, or when only a flagellar beat can be observed
Non-motile sperm: Sperm exhibiting no movement
Raw sample: Semen in its natural, untouched state 3. Test Overview Fresh human semen samples (aim to start processing within 60 min from collection) were loaded to consumable prototypes, sample gates were opened and output samples were retrieved every 5 minutes from the Sperm Buffer compartment (=output) to assess the motile sperm's ability to swim across the device geometry. It was anticipated that short incubation periods would result in lower concentrations but increasingly more progressively motile sperm, whereas long periods would result in higher concentrations of sperm, but overall reduced progressive motility as compared to the earlier collected cohorts.

4. Test Materials

Semen samples were donated by consenting volunteer donors. The donors were men between 20 and 40 years of age with unknown fertility history, ie there were no attempts to ascertain their fertility status for the testing. The study was approved by the Human Ethics Committee of the applicant company.

All laboratory consumables (pipette tips, test tubes, microscope slides etc) were same as used in an IVF clinic and/or Andrology laboratories. Analysis of test parameters was performed using Computer Assisted Sperm Analysis (CASA) system, namely IVOS Version 12 (Hamilton Thorne) and Leja analysis slides (Leja).

Sperm separation device prototypes were manufactured on-site with 3D printer and washed thoroughly before use.

5. Test Method
Ensure that the device(s) and solutions to be used for tests are at 37 degrees Celsius
Assess the semen sample initial characteristics (concentration, progressive motility, concentration of progressively motile sperm)
Add 1% blue food dye into semen sample to dye it (dye tested to be safe and non-toxic, the purpose being to assist in detection of leaks)
Load each device with 500 μL of semen in the Sample Compartment followed by the loading of 250 μL of Sperm Buffer in Buffer Compartment. Note: Ensure device gate is in its closed setting prior the loading.
For the pre-sort reading collect the sample for reading (~4 μL) from the Sample Compartment and assess with CASA
Open the device gate and start timer (Note: do not delay starting the opening of the device in virtue of the semen reading)
Collect a sample from Buffer Compartment (=time 0') for reading (~4 μL) and assess with CASA
Repeat sample collection from Buffer Compartment every 5 minutes until 25 minutes has passed, while maintaining the device at 37 degrees Celsius
At that time, close the device gate and extract total remaining volume of buffer from Buffer Compartment (=full volume output)
Measure the extracted volume
Throughout the testing, take note of changes in colour of the Buffer Compartment and record. If leaking happens the Sperm Buffer will acquire different shades of blue (the darker, larger the leak).
Analyse the results.

6. Test Results

Table 1, below, presents the results of 12 tests acquired on two separate days with samples from three different donors, utilizing two different device prototypes (based on the first and second embodiments described above and labelled 'Stonehenge' and 'Twister', respectively). Mean values and Standard Deviations are presented of Sperm Concentration (million sperm per mL), Progressive Motility (% of sperm exhibiting progressive movement) and Concentration of Progressively Motile Sperm (million progressively motile sperm per mL).

The last value is the defining factor when assessing whether the processed sperm sample is suitable to be used for IVF, although the target value varies between clinics and is dependent on the type of fertilisation procedure used at the clinic. For example, if fertilization of oocytes takes place in a microdrop (10-50 μL), higher concentration is usually required as opposed to fertilization in a microwell (300-700 μL).

Buffer Compartment would have been measured. However, the pattern observed is still relevant for these tests.

Progressive motility of the semen sample before sorting varied between 10 and 55%, which represents values both below and above WHO defined lower reference limit of 32%. These figures did not however reflect the initial quality of the original sample (range 11-66% soon after collection), but rather the quality of the sample at the start of processing, at which point the age of the sample varied between 35 and 177 min. It is known that progressive motility of sperm decreases over time, and a recommended clinical practice is to process semen sample within 60 min of collection.

During processing this value increased from the initial 24 to 28% to the peaks of 71% (Stonehenge) and 89% (Twister), from there to reduce again in both device designs

TABLE 1

Semen processing and sorting outcomes with two different device design prototypes over an extended processing time

| Device design | Value | Pre-sort | 0' | 5' | 10' | 15' | 20' | 25' | 25' (full vol) |
|---|---|---|---|---|---|---|---|---|---|
| Sperm Concentration M/mL | | | | | | | | | |
| Stonehenge | (mean) | 64.6 | 0.4 | 0.5 | 1.2 | 7.5 | 2.2 | 3.1 | 16.9 |
|  | (SD) | 18.1 | 0.4 | 0.2 | 0.7 | 11.4 | 1.4 | 2.0 | 17.4 |
| Twister | (mean) | 59.7 | 0.2 | 0.5 | 1.5 | 2.5 | 5.7 | 6.6 | 19.4 |
|  | (SD) | 7.3 | 0.2 | 0.3 | 1.5 | 2.0 | 7.3 | 9.3 | 20.8 |
| Progressive Motility % | | | | | | | | | |
| Stonehenge | (mean) | 37 | 28 | 36.8 | 50.8 | 60.3 | 71 | 66 | 43.3 |
|  | (SD) | 15.2 | 20.6 | 15.0 | 24.5 | 24.0 | 27.6 | 22.5 | 22.6 |
| Twister | (mean) | 38.5 | 24.2 | 36.8 | 89.3 | 75.7 | 88.3 | 85.2 | 71.5 |
|  | (SD) | 11.9 | 19.4 | 24.7 | 12.5 | 22.8 | 5.2 | 14.6 | 25.0 |
| Concentration of Progressively Motile Sperm M/mL | | | | | | | | | |
| Stonehenge | (mean) | 10.92 | Nd | 0.20 | 0.67 | 1.78 | 1.70 | 2.13 | 6.08 |
|  | (SD) | 3.8 | Nd | 0.1 | 0.7 | 0.9 | 1.3 | 1.5 | 4.3 |
| Twister | (mean) | 11.45 | Nd | 0.17 | 1.32 | 2.18 | 5.33 | 6.15 | 10.68 |
|  | (SD) | 4.1 | nd | 0.1 | 1.3 | 2.1 | 7.0 | 8.9 | 7.8 |

Figure 32:
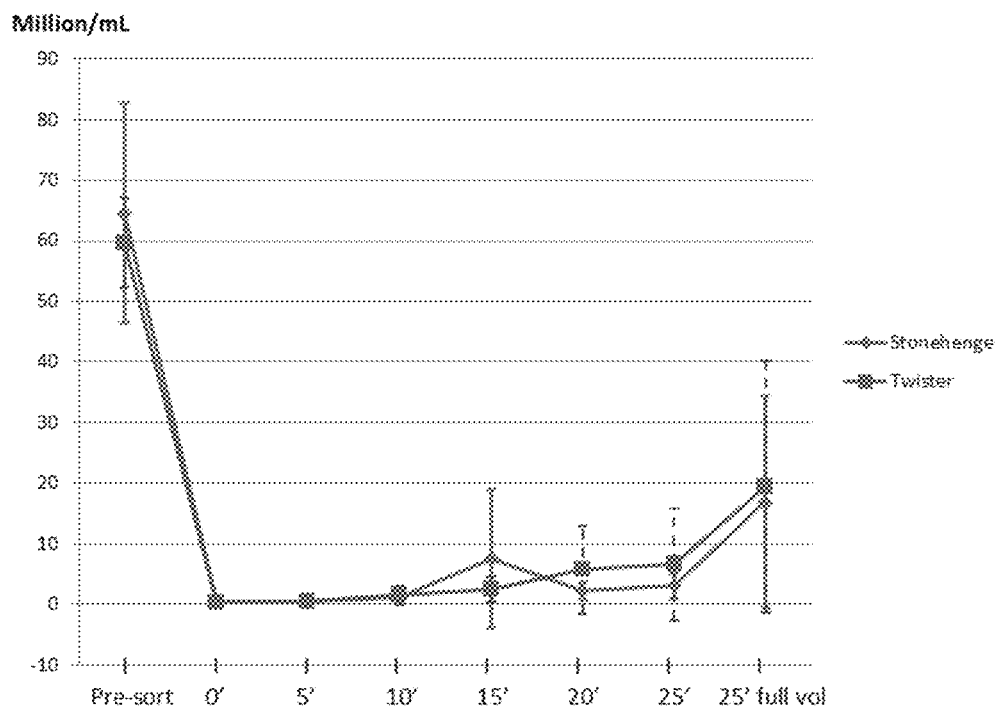
FIG. 32 is a chart showing sorted sperm concentration outcomes with two different device design prototypes over an extended processing time (mean & SD).
Figure 33:
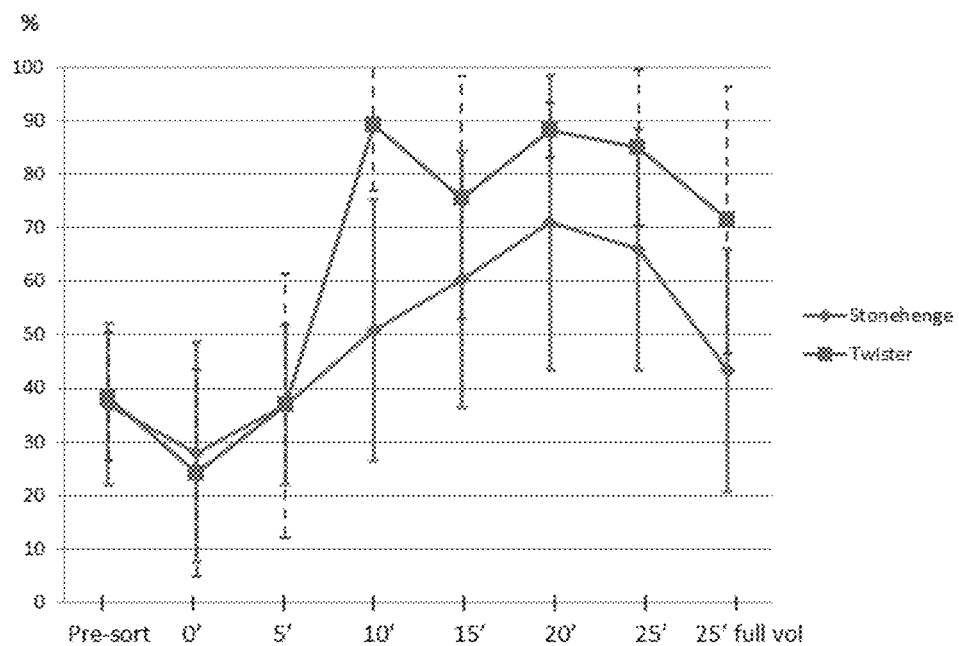
FIG. 33 is a chart showing sorted sperm progressive motility outcomes with two different device design prototypes over an extended processing time (mean & SD).
Figure 34:
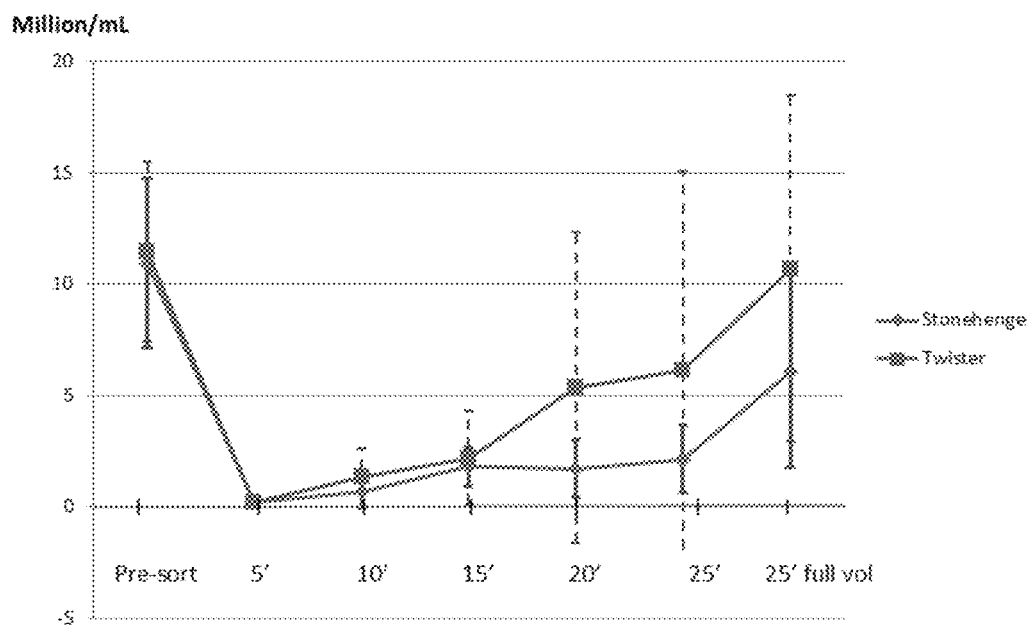
FIG. 34 is a chart showing sorted progressively motile sperm concentration outcomes with two different device design prototypes over an extended processing time (mean & SD).

To better illustrate the changes in the sperm parameters over time, FIGS. 32, 33, and 34 show the results in graph format.

7. Discussion

As can be expected, total concentrations of sperm were higher in the pre-sorting samples than post-sorting. All the donated samples in these tests before sorting had total sperm concentrations above WHO defined lower reference limits for semen characteristics (WHO 2015 5$^{th}$ Edition), i.e could be considered 'normal' (sample range 59-101 M/mL, WHO lower reference limit 15 M/mL).

Sperm output concentrations increased over the duration of the processing, being understandably highest at 25 minutes time point (Table 1 and Plot A). Interestingly, the "full volume" output showed even higher concentration than the initial sampling volume at that same time point, most likely reflecting inaccuracies in sampling due to small sampling volumes, and possibly also uneven distribution of sperm in the Buffer Compartment during processing.

All other time point results were based on only 4 μL samples whereas the final full volume sample consisted of total output and ranged between 50 and 100 μL. Hence it is possible that the earlier time points may not have accurately reflected the actual concentration of sperm at that particular time point, and the concentration might have been somewhat different, possibly higher, if the whole output volume in the (Table 1 and Plot B). The values over 60% can be used or clinical IVF, although ideally the progressive motility percentage should be 80-90%.

The reduction in progressive motility at 25' is likely related to increasing number (and concentration) of sperm as the Buffer Compartment started to get saturated. In those conditions, it is possible that in addition to most motile sperm population, also some less motile sperm might have had enough time to move from Sample Compartment to Buffer Compartment, thus reducing the overall progressive motility percentage.

The final determinant for clinical usability of the processed sample is the concentration of progressively motile sperm, a combination of the previous two values. It is reassuring to see that this value increased gradually over time from pre-sorting mean values of approx. 11 M/mL to 6 (Stonehenge) or 11 (Twister) M/mL. Although the overall value was not drastically different pre- and post-sorting in these particular tests, it still represents the portion of washed sperm removed from seminal plasma and as such the portion immediately suitable for clinical use.

As can be seen from the results, Standard Deviations were high, representing large variations in outcomes between the tests. Whether this was due to characteristics of the samples themselves, or the differences between time points or device designs, is difficult to say at this point. However, the overall conclusions suggest that both designs lead to suitable sperm processing outcomes, although in this set of tests the Twister design appears more promising than Stonehenge.

In regards to optimal duration of the process, both sperm total concentration and progressive motility seem to plateau after about 10 to 15 minutes, at least if considering only the results of the sampled small volumes. This time is considerably faster than what can be achieved with traditional Density Gradient Centrifugation.

The following sections I-VII provide a guide to interpreting the present specification.

I. Terms

The term "product" means any machine, manufacture and/or composition of matter, unless expressly specified otherwise.

The term "process" means any process, algorithm, method or the like, unless expressly specified otherwise.

Each process (whether called a method, algorithm or otherwise) inherently includes one or more steps, and therefore all references to a "step" or "steps" of a process have an inherent antecedent basis in the mere recitation of the term 'process' or a like term. Accordingly, any reference in a claim to a 'step' or 'steps' of a process has sufficient antecedent basis.

The term "invention" and the like mean "the one or more inventions disclosed in this specification", unless expressly specified otherwise.

The terms "an embodiment", "embodiment", "embodiments", "the embodiment", "the embodiments", "one or more embodiments", "some embodiments", "certain embodiments", "one embodiment", "another embodiment" and the like mean "one or more (but not all) embodiments of the disclosed invention(s)", unless expressly specified otherwise.

The term "variation" of an invention means an embodiment of the invention, unless expressly specified otherwise.

A reference to "another embodiment" in describing an embodiment does not imply that the referenced embodiment is mutually exclusive with another embodiment (e.g., an embodiment described before the referenced embodiment), unless expressly specified otherwise.

The terms "including", "comprising" and variations thereof mean "including but not limited to", unless expressly specified otherwise.

The terms "a", "an" and "the" mean "one or more", unless expressly specified otherwise.

The term "plurality" means "two or more", unless expressly specified otherwise.

The term "herein" means "in the present specification, including anything which may be incorporated by reference", unless expressly specified otherwise.

The phrase "at least one of", when such phrase modifies a plurality of things (such as an enumerated list of things), means any combination of one or more of those things, unless expressly specified otherwise. For example, the phrase "at least one of a widget, a car and a wheel" means either (i) a widget, (ii) a car, (iii) a wheel, (iv) a widget and a car, (v) a widget and a wheel, (vi) a car and a wheel, or (vii) a widget, a car and a wheel. The phrase "at least one of", when such phrase modifies a plurality of things, does not mean "one of each of" the plurality of things.

Numerical terms such as "one", "two", etc. when used as cardinal numbers to indicate quantity of something (e.g., one widget, two widgets), mean the quantity indicated by that numerical term, but do not mean at least the quantity indicated by that numerical term. For example, the phrase "one widget" does not mean "at least one widget", and therefore the phrase "one widget" does not cover, e.g., two widgets.

The phrase "based on" does not mean "based only on", unless expressly specified otherwise. In other words, the phrase "based on" describes both "based only on" and "based at least on". The phrase "based at least on" is equivalent to the phrase "based at least in part on".

The term "represent" and like terms are not exclusive, unless expressly specified otherwise. For example, the term "represents" do not mean "represents only", unless expressly specified otherwise. In other words, the phrase "the data represents a credit card number" describes both "the data represents only a credit card number" and "the data represents a credit card number and the data also represents something else".

The term "whereby" is used herein only to precede a clause or other set of words that express only the intended result, objective or consequence of something that is previously and explicitly recited. Thus, when the term "whereby" is used in a claim, the clause or other words that the term "whereby" modifies do not establish specific further limitations of the claim or otherwise restricts the meaning or scope of the claim.

The term "e.g." and like terms mean "for example", and thus does not limit the term or phrase it explains. For example, in the sentence "the computer sends data (e.g., instructions, a data structure) over the Internet", the term "e.g." explains that "instructions" are an example of "data" that the computer may send over the Internet, and also explains that "a data structure" is an example of "data" that the computer may send over the Internet. However, both "instructions" and "a data structure" are merely examples of "data", and other things besides "instructions" and "a data structure" can be "data".

The term "i.e." and like terms mean "that is", and thus limits the term or phrase it explains. For example, in the sentence "the computer sends data (i.e., instructions) over the Internet", the term "i.e." explains that "instructions" are the "data" that the computer sends over the Internet.

Any given numerical range shall include whole and fractions of numbers within the range. For example, the range "1 to 10" shall be interpreted to specifically include whole numbers between 1 and 10 (e.g., 2, 3, 4, . . . 9) and non-whole numbers (e.g., 1.1, 1.2, . . . 1.9).

II. Determining

The term "determining" and grammatical variants thereof (e.g., to determine a price, determining a value, determine an object which meets a certain criterion) is used in an extremely broad sense. The term "determining" encompasses a wide variety of actions and therefore "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing, and the like.

The term "determining" does not imply certainty or absolute precision, and therefore "determining" can include estimating, extrapolating, predicting, guessing and the like.

The term "determining" does not imply that mathematical processing must be performed, and does not imply that numerical methods must be used, and does not imply that an algorithm or process is used.

The term "determining" does not imply that any particular device must be used. For example, a computer need not necessarily perform the determining.

The term "buffer" may refer to buffer or media and is used indiscriminately herein. For example, further definition of a "buffer" may include a description of aqueous solution of compositions of matter such as salts, proteins, sugars, or other compounds.

III. Indication

The term "indication" is used in an extremely broad sense. The term "indication" may, among other things, encompass a sign, symptom, or token of something else.

The term "indication" may be used to refer to any indicia and/or other information indicative of or associated with a subject, item, entity, and/or other object and/or idea.

As used herein, the phrases "information indicative of" and "indicia" may be used to refer to any information that represents, describes, and/or is otherwise associated with a related entity, subject, or object.

Indicia of information may include, for example, a symbol, a code, a reference, a link, a signal, an identifier, and/or any combination thereof and/or any other informative representation associated with the information.

In some embodiments, indicia of information (or indicative of the information) may be or include the information itself and/or any portion or component of the information. In some embodiments, an indication may include a request, a solicitation, a broadcast, and/or any other form of information gathering and/or dissemination.

IV. Forms of Sentences

Where a limitation of a first claim would cover one of a feature as well as more than one of a feature (e.g., a limitation such as "at least one widget" covers one widget as well as more than one widget), and where in a second claim that depends on the first claim, the second claim uses a definite article "the" to refer to the limitation (e.g., "the widget"), this does not imply that the first claim covers only one of the feature, and this does not imply that the second claim covers only one of the feature (e.g., "the widget" can cover both one widget and more than one widget).

When an ordinal number (such as "first", "second", "third" and so on) is used as an adjective before a term, that ordinal number is used (unless expressly specified otherwise) merely to indicate a particular feature, such as to distinguish that particular feature from another feature that is described by the same term or by a similar term. For example, a "first widget" may be so named merely to distinguish it from, e.g., a "second widget". Thus, the mere usage of the ordinal numbers "first" and "second" before the term "widget" does not indicate any other relationship between the two widgets, and likewise does not indicate any other characteristics of either or both widgets. For example, the mere usage of the ordinal numbers "first" and "second" before the term "widget" (1) does not indicate that either widget comes before or after any other in order or location; (2) does not indicate that either widget occurs or acts before or after any other in time; and (3) does not indicate that either widget ranks above or below any other, as in importance or quality. In addition, the mere usage of ordinal numbers does not define a numerical limit to the features identified with the ordinal numbers. For example, the mere usage of the ordinal numbers "first" and "second" before the term "widget" does not indicate that there must be no more than two widgets.

When a single device or article is described herein, more than one device/article (whether or not they cooperate) may alternatively be used in place of the single device/article that is described. Accordingly, the functionality that is described as being possessed by a device may alternatively be possessed by more than one device/article (whether or not they cooperate).

Similarly, where more than one device or article is described herein (whether or not they cooperate), a single device/article may alternatively be used in place of the more than one device or article that is described. For example, a plurality of computer-based devices may be substituted with a single computer-based device. Accordingly, the various functionality that is described as being possessed by more than one device or article may alternatively be possessed by a single device/article.

The functionality and/or the features of a single device that is described may be alternatively embodied by one or more other devices which are described but are not explicitly described as having such functionality/features. Thus, other embodiments need not include the described device itself, but rather can include the one or more other devices which would, in those other embodiments, have such functionality/features.

V. Disclosed Examples and Terminology Are Not Limiting

Neither the Title nor the Abstract in this specification is intended to be taken as limiting in any way as the scope of the disclosed invention(s). The title and headings of sections provided in the specification are for convenience only, and are not to be taken as limiting the disclosure in any way.

Numerous embodiments are described in the present application, and are presented for illustrative purposes only. The described embodiments are not, and are not intended to be, limiting in any sense. The presently disclosed invention(s) are widely applicable to numerous embodiments, as is readily apparent from the disclosure. One of ordinary skill in the art will recognise that the disclosed invention(s) may be practised with various modifications and alterations, such as structural, logical, software, and electrical modifications. Although particular features of the disclosed invention(s) may be described with reference to one or more particular embodiments and/or drawings, it should be understood that such features are not limited to usage in the one or more particular embodiments or drawings with reference to which they are described, unless expressly specified otherwise.

The present disclosure is not a literal description of all embodiments of the invention(s). Also, the present disclosure is not a listing of features of the invention(s) which must be present in all embodiments.

Devices that are described as in communication with each other need not be in continuous communication with each other, unless expressly specified otherwise. On the contrary, such devices need only transmit to each other as necessary or desirable, and may actually refrain from exchanging data most of the time. For example, a machine in communication with another machine via the Internet may not transmit data to the other machine for long period of time (e.g. weeks at a time). In addition, devices that are in communication with each other may communicate directly or indirectly through one or more intermediaries. Similar meanings applies mutatis mutandi for devices or components that are described as in fluid or liquid communication with each other.

A description of an embodiment with several components or features does not imply that all or even any of such components/features are required. On the contrary, a variety of optional components are described to illustrate the wide variety of possible embodiments of the present invention(s). Unless otherwise specified explicitly, no component/feature is essential or required.

Although process steps, operations, algorithms or the like may be described in a particular sequential order, such processes may be configured to work in different orders. In other words, any sequence or order of steps that may be explicitly described does not necessarily indicate a requirement that the steps be performed in that order. The steps of processes described herein may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to the invention(s), and does not imply that the illustrated process is preferred.

Although a process may be described as including a plurality of steps, that does not imply that all or any of the steps are preferred, essential or required. Various other embodiments within the scope of the described invention(s) include other processes that omit some or all of the described steps. Unless otherwise specified explicitly, no step is essential or required.

Although a process may be described singly or without reference to other products or methods, in an embodiment the process may interact with other products or methods. For example, such interaction may include linking one business model to another business model. Such interaction may be provided to enhance the flexibility or desirability of the process.

Although a product may be described as including a plurality of components, aspects, qualities, characteristics and/or features, that does not indicate that any or all of the plurality are preferred, essential or required. Various other embodiments within the scope of the described invention(s) include other products that omit some or all of the described plurality.

An enumerated list of items (which may or may not be numbered) does not imply that any or all of the items are mutually exclusive, unless expressly specified otherwise. Likewise, an enumerated list of items (which may or may not be numbered) does not imply that any or all of the items are comprehensive of any category, unless expressly specified otherwise. For example, the enumerated list "a computer, a laptop, a PDA" does not imply that any or all of the three items of that list are mutually exclusive and does not imply that any or all of the three items of that list are comprehensive of any category.

An enumerated list of items (which may or may not be numbered) does not imply that any or all of the items are equivalent to each other or readily substituted for each other.

All embodiments are illustrative, and do not imply that the invention or any embodiments were made or performed, as the case may be.

VI. Computing

It will be readily apparent to one of ordinary skill in the art that the various processes described herein may be implemented by, e.g., appropriately programmed general purpose computers, special purpose computers and computing devices. Typically a processor (e.g., one or more microprocessors, one or more micro-controllers, one or more digital signal processors) will receive instructions (e.g., from a memory or like device), and execute those instructions, thereby performing one or more processes defined by those instructions.

A "processor" means one or more microprocessors, central processing units (CPUs), computing devices, microcontrollers, digital signal processors, or like devices or any combination thereof.

Thus a description of a process is likewise a description of an apparatus for performing the process. The apparatus that performs the process can include, e.g., a processor and those input devices and output devices that are appropriate to perform the process.

Further, programs that implement such methods (as well as other types of data) may be stored and transmitted using a variety of media (e.g., computer readable media) in a number of manners. In some embodiments, hard-wired circuitry or custom hardware may be used in place of, or in combination with, some or all of the software instructions that can implement the processes of various embodiments. Thus, various combinations of hardware and software may be used instead of software only.

The term "computer-readable medium" refers to any medium, a plurality of the same, or a combination of different media, that participate in providing data (e.g., instructions, data structures) which may be read by a computer, a processor or a like device. Such a medium may take many forms, including but not limited to, non-volatile media, volatile media, and transmission media. Non-volatile media include, for example, optical or magnetic disks and other persistent memory. Volatile media include dynamic random access memory (DRAM), which typically constitutes the main memory. Transmission media include coaxial cables, copper wire and fibre optics, including the wires that comprise a system bus coupled to the processor. Transmission media may include or convey acoustic waves, light waves and electromagnetic emissions, such as those generated during radio frequency (RF) and infra-red (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, a carrier wave as described hereinafter, or any other medium from which a computer can read.

Various forms of computer readable media may be involved in carrying data (e.g. sequences of instructions) to a processor. For example, data may be (i) delivered from RAM to a processor; (ii) carried over a wireless transmission medium; (iii) formatted and/or transmitted according to numerous formats, standards or protocols, such as Ethernet (or IEEE 802.3), SAP, ATP, Bluetooth™, and TCP/IP, TDMA, CDMA, and 3G; and/or (iv) encrypted to ensure privacy or prevent fraud in any of a variety of ways well known in the art.

Thus a description of a process is likewise a description of a computer-readable medium storing a program for performing the process. The computer-readable medium can store (in any appropriate format) those program elements which are appropriate to perform the method.

Just as the description of various steps in a process does not indicate that all the described steps are required, embodiments of an apparatus include a computer/computing device operable to perform some (but not necessarily all) of the described process.

Likewise, just as the description of various steps in a process does not indicate that all the described steps are required, embodiments of a computer-readable medium storing a program or data structure include a computer-readable medium storing a program that, when executed, can cause a processor to perform some (but not necessarily all) of the described process.

Where databases are described, it will be understood by one of ordinary skill in the art that (i) alternative database structures to those described may be readily employed, and (ii) other memory structures besides databases may be readily employed. Any illustrations or descriptions of any sample databases presented herein are illustrative arrangements for stored representations of information. Any number of other arrangements may be employed besides those suggested by, e.g., tables illustrated in drawings or elsewhere. Similarly, any illustrated entries of the databases represent exemplary information only; one of ordinary skill in the art will understand that the number and content of the entries can be different from those described herein. Further, despite any depiction of the databases as tables, other formats (including relational databases, object-based models and/or distributed databases) could be used to store and manipulate the data types described herein. Likewise, object methods or behaviours of a database can be used to implement various processes, such as the described herein. In addition, the databases may, in a known manner, be stored locally or remotely from a device which accesses data in such a database.

Various embodiments can be configured to work in a network environment including a computer that is in communication (e.g., via a communications network) with one or more devices. The computer may communicate with the devices directly or indirectly, via any wired or wireless medium (e.g. the Internet, LAN, WAN or Ethernet, Token Ring, a telephone line, a cable line, a radio channel, an optical communications line, commercial on-line service providers, bulletin board systems, a satellite communications link, a combination of any of the above). Each of the devices may themselves comprise computers or other computing devices that are adapted to communicate with the computer. Any number and type of devices may be in communication with the computer.

In an embodiment, a server computer or centralised authority may not be necessary or desirable. For example, the present invention may, in an embodiment, be practised on one or more devices without a central authority. In such an embodiment, any functions described herein as performed by the server computer or data described as stored on the server computer may instead be performed by or stored on one or more such devices.

Where a process is described, in an embodiment the process may operate without any user intervention. In another embodiment, the process includes some human intervention (e.g., a step is performed by or with the assistance of a human).

While this invention has been described in connection with specific embodiments thereof, it will be understood that it is capable of further modification(s). This application is intended to cover any variations uses or adaptations of the invention following in general, the principles of the invention and including such departures from the present disclosure as come within known or customary practice within the art to which the invention pertains and as may be applied to the essential features hereinbefore set forth.

As the present invention may be embodied in several forms without departing from the spirit of the essential characteristics of the invention, it should be understood that the above described embodiments are not to limit the present invention unless otherwise specified, but rather should be construed broadly within the spirit and scope of the invention as defined in the appended claims. The described embodiments are to be considered in all respects as illustrative only and not restrictive.

Various modifications and equivalent arrangements are intended to be included within the spirit and scope of the invention and appended claims. Therefore, the specific embodiments are to be understood to be illustrative of the many ways in which the principles of the present invention may be practiced. For example, the following embodiments also fall within the scope of the appended claims.

Based on embodiments as shown in the accompanying drawings, a fluid communication interface may be provided by a toothed gate is between sample and buffer volumes where a concentric arrangement of the volumes is provided in which the sample may be provided on the outside and the buffer disposed within the inside volume. (Equally, in an alternate form the two volumes may be disposed in a vice versa arrangement with buffer disposed on the outside volume.) The aperture opens upon rotation of a cam ring. A top component lifts on this action. Vertical apertures open between teeth at ~1:10 ratio of vertical travel. Sperm can swim along multiple trajectories to buffer through apertures. Semen is loaded (~1 mL) into the outside of volume of the device. The device is in the closed state with a seal between the teeth of the upper and lower parts.

Sperm buffer is loaded into the inside ring device. The device is in the closed state with a seal between the teeth of the upper and lower parts. The fill levels must be the same or slightly higher in the buffer level to avoid flow of neat semen into the inner sorting volume.

A fissure is created between the two fluids when the cam ring is rotated clockwise. The upper component is accordingly pushed up by ramps on the cam.

If required, teeth can be closed preventing diffusions of seminal plasma into the sperm buffer volume prior to aspiration of the sorted sperm.

As with other described embodiments, motile sperm can be aspirated with a pipette from the inner volume.

In an alternate embodiment, semen is loaded into the outside volume of the device. The device is in the closed state with a seal between the base component and a cylindrical top piece. Sperm buffer is loaded into the inside ring device. The device is in the closed state with a seal between the teeth of the upper and lower parts. The fill levels must be the same or slightly higher in the buffer level to avoid flow of neat semen into the inner sorting volume. Again, if required, teeth can be closed preventing diffusions of seminal plasma into the sperm buffer volume prior to aspiration of the sorted sperm and motile sperm can be aspirated with a pipette from the inner volume.

In the following claims, means-plus-function clauses are intended to cover structures as performing the defined function and not only structural equivalents, but also equivalent structures. For example, although a nail and a screw may not be structural equivalents in that a nail employs a cylindrical surface to secure wooden parts together, whereas a screw employs a helical surface to secure wooden parts together, in the environment of fastening wooden parts, a nail and a screw are equivalent structures.

It should be noted that where the terms "server", "secure server" or similar terms are used herein, a communication device is described that may be used in a communication system, unless the context otherwise requires, and should not be construed to limit the present invention to any particular communication device type. Thus, a communication device may include, without limitation, a bridge, router, bridge-router (router), switch, node, or other communication device, which may or may not be secure.

It should also be noted that where a flowchart is used herein to demonstrate various aspects of the invention, it should not be construed to limit the present invention to any particular logic flow or logic implementation. The described logic may be partitioned into different logic blocks (e.g., programs, modules, functions, or subroutines) without changing the overall results or otherwise departing from the true scope of the invention. Often, logic elements may be added, modified, omitted, performed in a different order, or implemented using different logic constructs (e.g., logic gates, looping primitives, conditional logic, and other logic constructs) without changing the overall results or otherwise departing from the true scope of the invention.

"Comprises/comprising" and "includes/including" when used in this specification is taken to specify the presence of stated features, integers, steps or components but does not preclude the presence or addition of one or more other features, integers, steps, components or groups thereof. Thus, unless the context clearly requires otherwise, throughout the description and the claims, the words 'comprise', 'comprising', 'includes', 'including' and the like are to be construed in an inclusive sense as opposed to an exclusive or exhaustive sense; that is to say, in the sense of "including, but not limited to".

We claim:

1. A method of processing a semen sample comprising the steps of: introducing the semen sample into a first fluid volume disposed adjacent a second fluid volume comprising buffer solution; wherein the first and second fluid volumes are open to the atmosphere and adapted-for fluid communication therebetween; filling the first and second fluid volumes with the semen sample and buffer solution, respectively, to a level of volume such that no net fluid transport can occurs between the fluid volumes; selectively separating the first fluid volume from the second fluid volume with a movable closure member disposed therebetween; wherein the step of selectively separating the first fluid volume from the second fluid volume comprises moving the closure member so that a fluid communication aperture is formed by one or a combination of the closure member or the closure member in combination with the first and second fluid volumes to allow fluid communication between the first fluid volume and the second fluid volume such that motile sperm migrate from the semen sample in the first fluid volume to the buffer solution in the second fluid volume.

2. The method as claimed in claim 1, wherein the dimensions of the fluid communication aperture are proportional to the displacement of the closure member.

3. The method as claimed in claim 1 further comprising the step of:
conducting visual analysis of the sperm that has entered the second fluid volume of buffer solution.

4. The method as claimed in claim 3 wherein the step of conducting visual analysis is conducted concurrently with the sperm entering the second fluid volume.

5. Apparatus for processing a semen sample comprising: i) a first well comprising a first fluid volume adapted for accommodating the semen sample; ii) a second well comprising a second fluid volume adapted for accommodating buffer solution where the first and second wells are adapted for fluid communication therebetween, and wherein the first and second fluid volumes are open to the atmosphere; iii) a movable closure member disposed between the first and second wells, configured for selectively separating the first fluid volume from the second fluid volume; wherein movement of the closure member with respect to the first and second fluid volumes forms a fluid communication aperture is configured to allow fluid communication between the first fluid volume and the second fluid volume such that motile sperm migrate from the semen sample in the first fluid volume to the buffer solution in the second fluid volume.

6. The apparatus as claimed in claim 5 wherein the dimensions of the fluid communication aperture are proportional to the axial displacement of the closure member.

7. The apparatus as claimed in claim 5 further including a third well comprising a third fluid volume for accommodating progressive sperm.

8. The apparatus as claimed in claim 5, further comprising:
an optic path formed in the apparatus comprising a flow path for a thin film of fluid formed between two transparent windows orthogonally disposed to the optical path.

9. The apparatus as claimed in claim 8 further comprising:
a camera disposed in the optic path for conducting visual analysis of the sperm that has entered the second fluid volume of buffer solution.

10. A method of separating a biological component from a biological sample comprising the steps of: introducing the biological sample into a first fluid volume disposed adjacent to a second volume fluid comprising buffer solution, and wherein the first and second fluid volumes are open to the atmosphere; filling the first and second fluid volumes with the biological sample and buffer solution, respectively, to a level of volume such that no net fluid transport occurs between the fluid volumes; selectively separating the first fluid volume from the second fluid volume with a movable closure member disposed therebetween; wherein the step of selectively separating the first fluid volume from the second fluid volume comprises moving the closure member so that a fluid communication aperture is formed by one or a combination of the closure member or the closure member in combination with the first and second fluid volumes to allow fluid communication between the first fluid volume and the second fluid volume such that the biological component migrates from the biological sample in the first fluid volume to the buffer solution in the second fluid volume.

11. The method as claimed in claim 10, wherein the dimensions of the fluid communication aperture are proportional to the displacement of the closure member.

12. The method as claimed in claim 10 further comprising the step of:
conducting visual analysis of the biological component entering the second fluid volume of buffer solution.

13. The method as claimed in claim 12 wherein the step of conducting visual analysis is performed concurrently with the biological component entering the second fluid volume of buffer solution.

14. Apparatus adapted for processing a semen sample, said apparatus comprising:

processor means adapted to operate in accordance with a predetermined instruction set, said apparatus, in conjunction with said instruction set, being adapted to perform the method steps as claimed in claim 1.

15. Apparatus adapted for processing a biological component in a biological sample, said apparatus comprising:

processor means adapted to operate in accordance with a predetermined instruction set, said apparatus, in conjunction with said instruction set, being adapted to perform the method steps as claimed in claim 10.

16. A computer program product comprising:

a computer usable medium having computer readable program code and computer readable system code embodied on said medium for operation within a data processing system and adapted for processing a semen sample, said computer program product comprising:

computer readable code within said computer usable medium for performing the method steps as claimed in claim 1.

17. A computer program product comprising:

a computer usable medium having computer readable program code and computer readable system code embodied on said medium for operation within a data processing system and adapted for processing a biological component in a biological sample, said computer program product comprising:

computer readable code within said computer usable medium for performing the method steps as claimed in claim 10.

18. The method as claimed in claim 1, wherein the fluid communication between the first fluid volume and the second fluid volume allows for only diffusion-based mixing of the semen sample and the buffer solution.

19. The apparatus as claimed in claim 6 wherein the apparatus is adapted to provide for fluid communication between the first fluid volume and the second fluid volume that allows for only diffusion-based mixing of the semen sample and the buffer solution.

* * * * *